(12) United States Patent
Bulleit et al.

(10) Patent No.: US 11,657,176 B2
(45) Date of Patent: May 23, 2023

(54) BLOCKCHAIN-BASED MECHANISMS FOR SECURE HEALTH INFORMATION RESOURCE EXCHANGE

(71) Applicant: BBM Health LLC, Atlanta, GA (US)

(72) Inventors: Douglas A. Bulleit, Atlanta, GA (US); Bharat Chand Aluri, Atlanta, GA (US); Fred Thomas Danner, III, Colorado Springs, CO (US); Charles Clifton Miller, III, Pebble Beach, CA (US); Mark Lloyd Braunstein, New York, NY (US)

(73) Assignee: Health Blockchain Convergence, Inc., Tysons Corner, VA (US)

( * ) Notice: Subject to any disclaimer, the term of this patent is extended or adjusted under 35 U.S.C. 154(b) by 214 days.

(21) Appl. No.: 16/831,208

(22) Filed: Mar. 26, 2020

(65) Prior Publication Data

US 2020/0226285 A1 Jul. 16, 2020

Related U.S. Application Data

(63) Continuation-in-part of application No. 15/684,173, filed on Aug. 23, 2017, now Pat. No. 11,227,675.
(Continued)

(51) Int. Cl.
*G06Q 20/00* (2012.01)
*G06F 21/62* (2013.01)
(Continued)

(52) U.S. Cl.
CPC .......... *G06F 21/6245* (2013.01); *G06F 21/33* (2013.01); *G06F 21/602* (2013.01); *G06Q 50/265* (2013.01); *G16H 10/60* (2018.01)

(58) Field of Classification Search
CPC .... G06F 21/6245; G06F 21/33; G06F 21/602; G06Q 50/265; G16H 10/60; G16H 40/67
(Continued)

(56) References Cited

U.S. PATENT DOCUMENTS 5,987,232 A 11/1999 Tabuki
9,292,671 B1 * 3/2016 Robinson ................ G06F 21/31
(Continued)

FOREIGN PATENT DOCUMENTS

WO WO-2015152905 A1 * 10/2015 ......... G06Q 20/4014
WO WO-2015163608 A1 * 10/2015 ............ C08F 212/10
(Continued)

OTHER PUBLICATIONS

WO2015152905 (Year: 2014).*
(Continued)

*Primary Examiner* — Dante Ravetti
(74) *Attorney, Agent, or Firm* — Lee & Hayes, P.C.

(57) ABSTRACT

Technologies are disclosed herein to secure flexible access to the healthcare information resources (HIR) contained within electronic health records (EHR) systems. By managing access permissions with certified self-sovereign identities and distributed ledger techniques, HIR may be secured. Patients and other users may be registered to access a distributed ledger, such as a healthcare blockchain, employed to set, host and adjudicate permissions to access HIR. Authorized owners and/or patients with rights to their own HIR may be able to grant fine-grained and conditional access permissions to third-parties. Information transfers and transactions occurring according to these permissions may be logged within smart contracts incorporated in the healthcare blockchain.

19 Claims, 23 Drawing Sheets

Related U.S. Application Data

(60) Provisional application No. 62/378,539, filed on Aug. 23, 2016.

(51) Int. Cl.

| | | |
|---|---|---|
| *G16H 10/60* | (2018.01) | |
| *G06F 21/60* | (2013.01) | |
| *G06F 21/33* | (2013.01) | |
| *G06Q 50/26* | (2012.01) | |

(58) Field of Classification Search
USPC .................... 705/16, 21, 59; 380/44, 262
See application file for complete search history.

(56) References Cited

U.S. PATENT DOCUMENTS

| | | |
|---|---|---|
| 10,547,457 B1 | 1/2020 | Duccini et al. |
| 2014/0074638 A1 | 3/2014 | Shah |
| 2014/0108046 A1 | 4/2014 | Echeverria Cabrera et al. |
| 2015/0067800 A1 | 3/2015 | Hosoda |
| 2015/0205929 A1 | 7/2015 | Brama |
| 2018/0060496 A1 | 3/2018 | Bulleit et al. |
| 2018/0117446 A1 | 5/2018 | Tran et al. |

FOREIGN PATENT DOCUMENTS

| | | | |
|---|---|---|---|
| WO | WO2015175722 | 11/2015 | |
| WO | WO2015179020 | 11/2015 | |
| WO | WO-2016163608 A1 * | 10/2016 | ........... G06Q 20/065 |
| WO | WO2018039312 A1 | 3/2018 | |

OTHER PUBLICATIONS

WO2016163608 (Year: 2016).*
U.S. Office Action dated Jul. 15, 2020 for U.S. Appl. No. 15/684,173, "Blockchain-Based Mechanisms for Secure Health Information Resource Exchange", Bulleit, 28 pages.
Australian Office Action dated Nov. 16, 2021 for Australian Patent Application No. 2017315345, a foreign counterpart to U.S. Appl. No. 15/684,173, 6 pages.
Azaria, A. et al. "Medrec: Using blockchain for medical data access and permission management", In Open and Big Data (OBD), International Conference on, Aug. 22, 2016, IEEE, pp. 25-30.
Baars, "Towards Self-Sovereign Identity using Blockchain Technology", Master's thesis, University of Twente, 2016, 90 pages.
Nichol, et al, "Co-Creation of Trust for Healthcare: The Cryptocitizen Framework for Interoperability with Blockchain", ResearchGate, Jun. 2016, 9 pages.
PCT Search Report and Written Opinion dated Nov. 15, 2017 for PCT Application PCT/US17/48156, 8 pages.
Office Action for U.S. Appl. No. 15/684,173, dated Feb. 8, 2021, Bulleit, "Blockchain-Based Mechanisms for Secure Health Information Resource Exchange ", 37 Pages.
Canadian Office Action dated Oct. 3, 2022 for Canadian Patent Application No. 3033385, a foreign counterpart to U.S. Pat. No. 11,227,675, 5 pages.
Canadian Office Action dated Mar. 21, 2023 for Canadian Patent Application No. 3,033,385, a foreign counterpart to U.S. Pat. No. 11,227,675, 5 pages.
U.S. Office Action for U.S. Appl. No. 17/538,405, dated Jan. 18, 2023, Douglas A. Bulleit, "Blockchain-based Mechanisms for Secure Health Information Resource Exchange", 22 pages.

* cited by examiner

BLOCKCHAIN-BASED MECHANISMS FOR SECURE HEALTH INFORMATION RESOURCE EXCHANGE

CROSS REFERENCE TO RELATED APPLICATIONS

This application is a Continuation-In-Part application and claims the benefit under 35 U.S.C. § 120 of co-pending U.S. patent application Ser. No. 15/684,173, filed Aug. 23, 2017, which claims the benefit of U.S. Provisional Application No. 62/378,539 filed Aug. 23, 2016, which are incorporated, in their entirety, by reference herein.

BACKGROUND

Healthcare records containing vital information resources may be generated by a variety of entities, such as healthcare providers, pharmacies, patients, and others. These healthcare records, even if in electronic health record (EHR) form, may reside in a variety of locations, and may not be easily accessible to a variety of applications, current stakeholders, and/or other users of those healthcare records. At the same time, different systems for storing healthcare records may utilize their own mechanism for controlling and disbursing the health information resources (HIR) that are stored within their various EHRs. This may cause confusion among patients and other users of the healthcare data, as well as difficulty in accessing the healthcare data itself. In many cases, patients may have little to no control of their EHRs and/or HIRs that pertain to them. In some cases, new applications development that could benefit from accessing and managing HIR data may be effectively restricted within legacy EHR environments.

Additionally, there are regulations and laws directed to the privacy of healthcare data. For example, regulations embodied in the Health Insurance Portability and Accountability Act (HIPAA) of 1996 regulates the extent to which certain kinds of patients' protected health information (PHI) may be shared with third-parties and/or otherwise utilized without the patient's permission. As a result, entities that store healthcare records containing PHI have implemented proprietary mechanisms for compliance to these regulations and for managing them. Accordingly, there are a variety of different systems for managing EHRs, most of which are not easily interoperable with each other.

Furthermore, due to potential liability resulting from non-compliance with PHI handling regulations, practicing health systems (e.g., hospitals) often choose to control the full lifecycle of their EHRs, from birth to destruction of the HIR data within them. Thus, the HIRs, or the presentation thereof, may not be readily customized or otherwise accessible to patient needs or the needs of the users of the data. Further still, caretakers of the healthcare data, such as care providers within healthcare systems, may be burdened with the liability of managing and disbursing healthcare data, in many cases, distracting those entities from their core competencies, such as providing healthcare.

It is with respect to these considerations and others that the disclosure made herein is provided.

SUMMARY

The technologies disclosed herein provide functionality for enabling electronic access to protected health information (PHI) according to the wishes of a patient and/or other authorized parties including, but not limited to, the healthcare provider to whom the healthcare data may belong or is otherwise authorized under existing regulation. The patient or provider may designate who (e.g., individuals, entities, applications, etc.) may have permission to access his or her PHI and/or other health information resources (HIRs), typically found within electronic health records (EHRs), and may further place conditional stipulations (e.g., time periods, redactions, locations, number of views, device types, anonymity, etc.) by which a designee may access authorized PHI and/or other HIRs. HIRs may include Protected Health Information (PHI) as it is defined by the Health Insurance Portability and Accountability Act (HIPAA), Personally Identifiable Information as defined by the GAS Privacy Act and/or other sensitive information found within EHRs.

According to example embodiments, electronic healthcare records (EHRs) may reside at a resource system of an entity that has generated the healthcare record or has received the healthcare record, such as a hospital's resource system(s) for managing EHRs. These resource systems may be configured to provide PHI and/or other HIRs to an authorized user application according to a predefined standard. An application program interface (API), such as HL7's Fast Healthcare Interoperability Resources (FHIR) may reside on a front-end of the resource system to provide this predefined format for granular HIRs to a requesting and authorized user's client system.

According to example embodiments of the disclosure, a user (e.g., patient) may be able, via an application executing on his or her client system, set conditional permissions for his or her HIR. Through a user interface of the application, the user may be able to designate conditional permissions for a particular HIR, or collection of resources such as those typically contained in an existing EHR. These conditional permission(s) may be used to generate a permission grant that may be sent to a distributed ledger, or healthcare blockchain system, to invoke an executable smart contract within a healthcare blockchain. If the user is authorized to cause permissions to be written onto the blockchain's smart contracts, then the blockchain systems may incorporate (e.g., hash with prior blocks) a new block containing new and/or modified permissions, such as in the form of one or more smart contracts. This operations may be enabled by any suitable mechanism. For example, some implementations may use smart contracts and other implementations may not use smart contracts.

Smart contracts contained within the healthcare blockchain may operate using any suitable protocols to adjudicate and/or enable agreements between parties to execute according to those agreements as prescribed, specified, codified, verified, and/or enforced. These same smart contracts may be both self-executing and or self-enforcing. In example embodiments, a smart contract is used to determine whether access to an HIR should be granted to a requesting party. In this case, the smart contract may make this determination based upon, among other factors, the verification of a certified self-sovereign identity (CSI) of the requesting party, a CSI of the party owning the information, and permissions previously provided by the owning party. In example embodiments, the mechanisms described may determine whether the requested level of access is greater than what was previously permissioned. As an example, the platform may disallow a request to write encounter data, when permission was previously provided to merely read the encounter data.

According to example embodiments of the disclosure, permissions may be expressed within one or more smart contract(s) in the blockchain that designates and/or enables the permissioning of others, such as in a conditional manner, to access the HIR for which the permissions in the blockchain were generated. Once incorporated into the healthcare blockchain, the smart contract(s) may generate and/or send an indication to a client system of a permissioned party that he, she or it may access the HIR for which permissions have been granted. In example embodiments, only the most recent permission states, as incorporated in the healthcare blockchain, may be able to authorize access tokens. As a result, an immutable record of all activity may recorded in the blockchain while preserving near real-time patient control and/or ability to correct any mistakes of information transfer to client and other systems.

Upon receiving an indication that a user (e.g., doctor, pharmacy, insurance company, researcher, etc.) or user application is authorized to access particular HIR, that user application may request HIR for which permissions have been granted, according to example embodiments of the disclosure. In other example embodiments, a user may attempt unprompted access, such as without knowing if he or she already has access to the particular HIR. In either case, the client system of the permissioned user, via an application operating thereon, can cooperate with other entities to arrange the issuance of an access token, using which, the HIR may be obtained. In example embodiments, the access token may be generated by smart contracts, as incorporated in the healthcare blockchain, and representing permissions granted for the particular HIR being requested. In example embodiments, the creation of the access token may be recorded within the healthcare blockchain, thus maintaining an immutable journal of all access token creation and issuance events. In other cases, the access tokens may be generated by software and/or hardware separate from the smart contracts.

The access token, as received by a client system associated with a permissioned user, may then be sent, by the client system, to a resource system where the PHI resources and other HIR resides. Responsive to receiving the access token, the resource system may provide the requested HIR to the client system of the requesting user.

When a client system receives an HIR, the client system may confirm receipt of the transaction brokered by the blockchain. Using the confirmation, the blockchain may maintain a record, such as an immutable record, of transactions of healthcare resources, as well as metadata pertaining to requests, permissions, and access tokens granted, or the like.

A client system may be configured to interact with other systems of the HIR delivery infrastructure to establish certified self-sovereign identification (CSI) key pairs (e.g., unique public, private and symmetric keys operating isochronously on both client and server systems, etc.) for accessing the healthcare blockchain, as well as other systems. In some cases, the access, as allowed by the CSI infrastructure may be pseudonymous. This process may include the client system being directed to one or more value-added certificate authorization system(s) with which the client system, and a user thereon, interacts. The value-added certificate authorization system(s) may request information about a user for whom the CSI is to be established. This information, in some cases, may include his or her current or anticipated healthcare providers' identification. The value-added certificate authorization system(s) may receive information about the user and/or his or her current or anticipated health providers' identification from the client system, as entered by the user thereon.

According to example embodiments, the value-added certificate authorization system(s) may verify the information about the user from an independent identity authority system. Based at least in part on the comparison of personal identity information supplied from the client system about the user and the corresponding information from and or other collaboration with the independent identity authority system and/or the resource system(s), the value-added certificate authorization system(s) may deem that the user is verified to be who he, she, or it claims to be. If the user is verified, then the value-added certificate authorization system(s) may digitally sign a verifiable claim attesting to the identity of the user.

Additionally or alternatively, the value-added certificate authorization system(s) may verify the information about the user by way of accessing a resource system on which the user may already have pre-existing health records. Further still, in an EHR issued digital certificate (EIDC) implementation, a user's identity may be verified by obtaining EHR resources from pre-existing health records and presenting challenge questions to the user based on those EHR resources. Thus, the resource systems on which the user's pre-existing health records are stored may be employed in the process of verifying the user's self-asserted identity.

The CSI is to be used subsequently by the client system and the user thereon to access HIRs to which the user may be entitled. In some cases, the access to the HIR, using the CSI may be pseudonymous. After the CSI is established, the value-added certificate authorization system(s) may direct the client system to an application download system and/or an application store to download a healthcare application onto the client system.

A client system may be configured to download and install a healthcare application from an application download system that the client device may access directly or be redirected from one or more other entities. The application download system may cooperate with the value-added certificate authorization system(s) to bind the public CSI of the user of the client system to the application that is downloaded and installed on the client system.

After the CSI establishment process, a process for binding a user, and his or her CSI, to the client system may be commenced. In some example embodiments, this process may involve various biometric and/or other multi-factor identification techniques and may result in the user being bound to the client device, and the user, with his or her CSI, bound to the healthcare blockchain. At this point, granting access to HIRS associated with the CSI of the user may be controlled by smart contracts, such as smart contracts residing on the healthcare blockchain.

The healthcare application may be installed on the client device, and it will then create it's own CSI. This may entail storing the CSI key pair, hash thereof, and/or other identifying information about the healthcare application in a digital wallet and/or other modules on the client device. Once the CSI is stored and bound to the healthcare application, the healthcare application operating on the client device may interact with the value-added certificate authorization system(s) to establish permissions for healthcare resources for which the user owns rights (e.g., the user's patient data). The permissions may, in some cases, be granulated and/or with conditions and/or stipulations. When permissions are established, a permission command indicating the permissions may be generated and sent to the blockchain systems for incorporation into the appropriate smart contract permission held within the healthcare blockchain. In some example embodiments, the establishment of permissions may be communicated to other entities, such as resource system(s) that have the HIRs for which permissions were established, as well as the value-added certificate authorization system(s), and/or other client systems associated with other users that have been granted permissions to the healthcare records.

In example embodiments, the permissions granted by a patient to access specific HIR may be highly granular, and may allow for conditions and/or stipulations. For example, the permissions may not only indicate who or what is allowed to access particular medical records' resources (e.g., HIRs), but also when those records may be accessed, if any parts must be redacted, if those records are to be anonymized, etc.

According to further example embodiments of the disclosure, the HIR, as provided from the resource system to the client system, may be relatively granular and adhere to a pre-designated format. The resource systems, in example embodiments, may have a front-end application programming interface (API) that may be universal and known to application developers, so that different application developers may develop healthcare applications for the client devices that may be able to interface with the resource systems in a pre-established manner.

In some example embodiments, a stake-holder or user (e.g., patient, pharmacist, etc.) may assert his or her identity and that identity may need to be verified to grant the user access to protected health records, such as EHRs. The verification of the self-asserted identity may be performed by the value-added certificate authorization system(s), which may be a single location system or set of distributed servers. In some cases, a claim of identity may be verified by any suitable mechanism, such as by verifying access to pre-established EHRs on resource system(s). In this mechanism, the value-added certificate authorization system(s) may identify a resource server where an EHR of a user who wishes to verify his or her identity is stored. If the EHR of the user is successfully accessed, then the value-added certificate authorization system(s) may indicate that the user's identity is verified.

In additional example embodiments, the value-added certificate authorization system(s) may verify a user's self-identity by identifying one or more EHRs of the user stored on one or more resource system(s). The value-added certificate authorization system(s) may generate access tokens to access the EHRs and/or data elements, referred to herein as EHR resources, and obtain the EHR resources form their respective resource system(s). The value-added certificate authorization system(s) may then generate questions (e.g., challenge questions) to present to the user who wishes to have his or her identity verified. These questions may be, for example, multiple choice questions or any other form of questioning. The value-added certificate authorization system(s) may cooperate with the user's client system to solicit and/or obtain answers to the questions. Depending on the answers to the questions, the value-added certificate authorization system(s) may indicate that the self-attested identity is verified, not verified, or requires additional questioning. A verified identity, or an indication thereof, may be registered with one or more blockchain system(s), thus allowing the user access and/or to set his or her permissions on his or her EHRs.

This Summary is provided to introduce a selection of concepts in a simplified form that are further described below in the Detailed Description. This Summary is not intended to identify all essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

The following detailed description is directed to providing a mechanism for improving security of storing and providing access to protected health information resource(s) HIR(s) (e.g., PHI) contained within electronic healthcare records (EHRs). It will be appreciated that the mechanism, as described herein, provides a greater level of trust between entities that control the lifecycle of healthcare record, including, for example, patients, healthcare providers, insurance companies, pharmacies, healthcare researchers, or the like. Furthermore, the mechanism, as described herein, may provide improved interoperability of entities that generate, maintain, provide, and consume HIR, as well as to provide information resource access to end-users and their chosen applications. Such mechanisms may reduce the cost of managing HIR, improve the efficiency of computing resources used in the maintenance and disbursement of medical records, and/or improve the transparency of healthcare records by maintaining immutable records.

Figure 1:
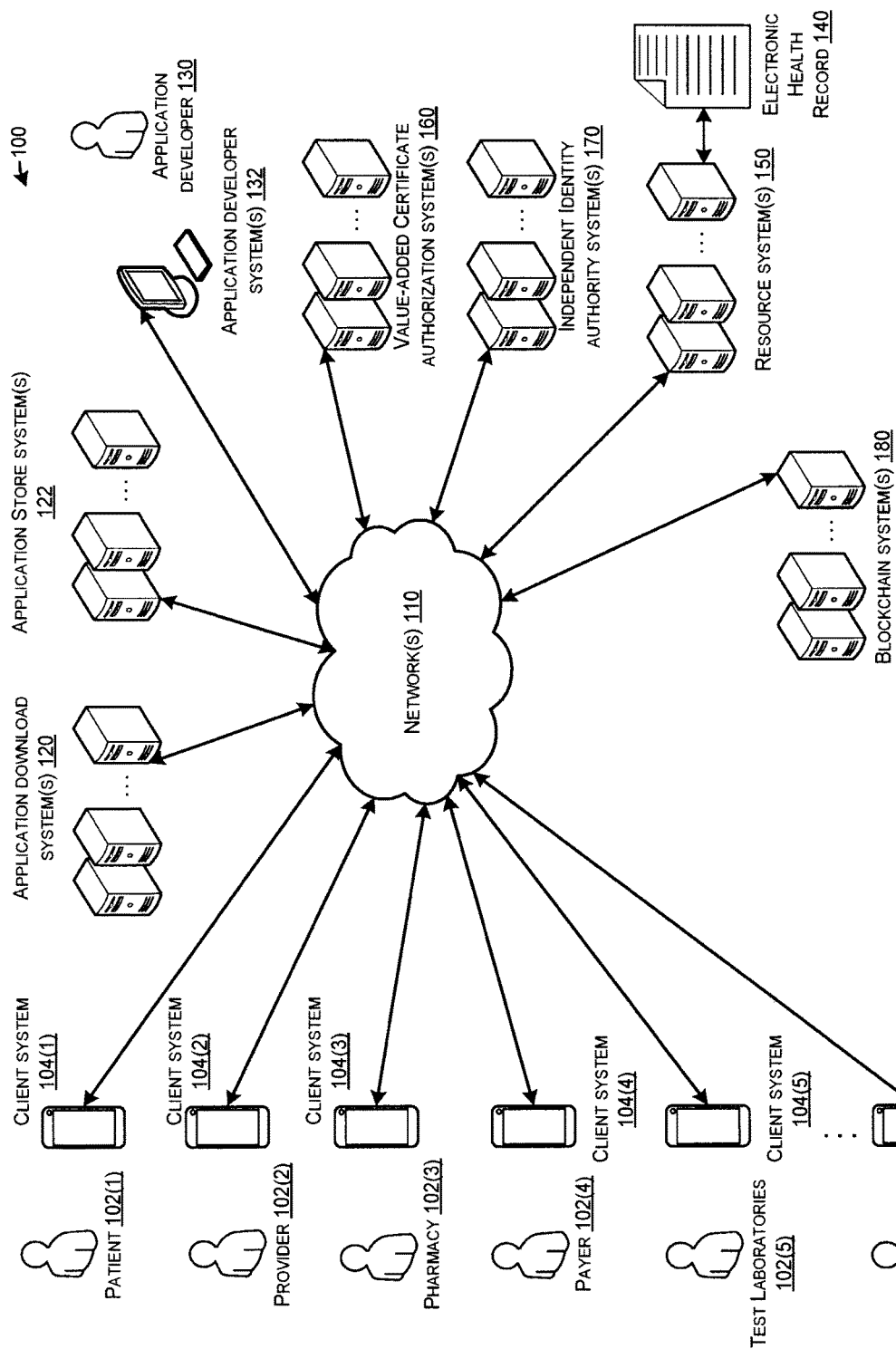
FIG. 1 is a schematic diagram showing an example environment including various entities that provide a mechanism of securing the distribution and permissioning of health information resource(s), according to example embodiments of the disclosure.

FIG. 1 is a schematic diagram showing an example environment 100 including various entities that provide a mechanism of securing the distribution and permissioning of health information resource(s), according to example embodiments of the disclosure. The various entities may be communicatively connected to each other via network(s) 110. The network(s) 110 may be any suitable type of network(s) 110, including but not limited to local area networks (LANs), wide area networks (WANs), proprietary networks, open networks, wired networks, Ethernet, wireless networks, the Internet, combinations thereof, or the like. The network(s) 110 may be configured to carry data, information, messages, or the like, such as in the form of data packets between any of the elements of the environment 100, using any suitable protocol, such as TCP/IP.

The environment may include various users, such as a patient 102(1), a healthcare provider 102(2), a pharmacy 102(3), a payer 102(4), a test laboratory 102(5), . . . , a researcher 102(N), or the like, referred to individually or collectively hereinafter as user 102. The users 102 may be one or more of consumers, generators, and/or owners of HIR, such as protected HIR stored in EHRs 140. The users may have respective client device(s) 104(1), 104(2), 104(3), 104(4), 104(5), . . . , 104(N), referred to individually or collectively hereinafter as a client device 104.

The client system(s) 104 may be configured to download and or install one or more healthcare applications that allow a user 102 to manage, process and/or obtain HIR. The client system 104 and the corresponding user 102 may interact with other entities of environment 100 to establish a certified self-sovereign identity (CSI) that may be used to obtain HIRs. The client system(s) 104 may be any suitable computing device, including, but not limited to, smartphones, telephones, tablets, smart televisions, set-top boxes, audio systems, imaging devices, computers, computing devices, netbook computers, notebook computers, smart watches, smart appliances, wearable computers, combinations thereof, or the like. Although all of the client systems 104 in environment 100 are depicted as smartphones, it will be appreciated that the client systems 104 may be of different types.

The environment 100 may include application stores and or download system(s) 120 that may be configured to provide one or more healthcare applications, such as applications that a user 102 may choose to install on his or her client system 104. In example embodiments, application download system(s) 120 may interact with other entities, such as value-added certificate authorization system(s) 160 and/or blockchain system(s) 180 to bind the CSI of the user 102 to his or her healthcare application(s) operating on his or her client system(s) 104. In some cases, the application download system(s) 120 may be accessed directly by the client systems 104, and in other cases, the client system 104 may be redirected to the application download system(s) 120 from other entities of environment 100, such as application store system(s) 122 and/or a value-added certificate authorization system(s) 160.

In example embodiments, if a user 102 attempts to download a healthcare application 104 from the application download system(s) 120, the application download system(s) 120 may verify whether the user has an established CSI. This verification may be performed by interacting with one or more other entities of the environment 100, such as the value-added certificate authorization system(s) 160 and or the blockchain itself 180. If the application download system(s) 120 determines that a user 102 attempting to download a healthcare application to his or her client system 104 has not yet established a valid CSI, then the application download system(s) 120 may redirect the session (e.g., via standard HTML redirect protocol) to the certificate authority system(s) 160 to first establish a CSI.

If during an attempted healthcare application download, the application download system(s) 120 determine that the user 102 has already established a CSI, then the application download system(s) 120 may cooperate with value-added certificate authorization system(s) 160 and blockchain system(s) 180 to bind the user's CSI to the healthcare application that is to be downloaded to the user's client system 104.

The environment 100 may include the application download system(s) 120 that may be configured to allow a user 102 to commence the download of one or more healthcare applications onto his or her client system 104. Examples of application download system(s) 120 may include system(s) associated with APPLE'S ITUNES, GOOGLE PLAY-STORE, various private stores (e.g., a hospital systems public and or internal portals), or indeed, any suitable application store.

The environment 100 may include resource system(s) 150 that may be an electronic health record (EHR) server configured to intake, store, and/or provide HIRs to authorized users 102. The resource system(s) 150 may be operated, controlled, and/or owned by one or more healthcare providers, independent repositories of HIR, pharmacies, insurers, research organizations, or indeed any suitable party. The resource system(s) 150 may be configured to provide a requested HIR to a requesting party, if that party is authorized to receive the requested HIR. The resource system(s) 150 may determine if a requesting party is authorized to receive requested HIR (e.g., PHI) by determining if a valid access token is received along with the request for the HIR.

The environment 100 may include an ecosystem of application developer system(s) 132 and corresponding application developer(s) 130. The environment 100, as described herein, allows for secure and standardized access to HIRs, as well as a mechanism for HIR providers, such as the entities that control the resource system(s) 150 to proactively manage liability associated with the management of the HIRs. Such an environment 100 with standardized access and liability management of HIRs, allows for the development of customized healthcare applications, such as by the application developer(s) 130.

As discussed with reference to the resource system(s) 150, where electronic HIRs 140 may be stored and managed, the HIR may be available to applications in a standardized format. In some cases, this standardized format may be highly granular in the type of HIR that is provided. This standardized and granular format of HIRs, as provided by API(s) allows for multiple application developers 130 to use standardized software development kits (SDKs) to build custom healthcare applications.

The HIRs 140 may include a variety of information regarding a patient 102(1) with which the HIR 140 is associated. In some cases, the information on the HIR 140 may be relatively rich, and may be a relatively good source of personal information for verifying a patient's identity. Indeed the HIRs 140 may include such information as name, date of birth, previous names, addresses, previous addresses, social security number, patient identifiers, unique patient identifiers, medical record numbers (MRNs), emergency contacts, parent's names, mother's maiden name, children's names, spouse's name, previous spouse(s) identifiers, driver's license number, previous driver's license information, passport number, citizenship information, previous citizenship(s), foreign nation(s) visited, current employer(s), previous employer(s), current educational institution(s) of affiliation, previous educational institution(s) attended, educational degree(s) granted, licenses and/or certificates granted, credit score, health insurance carrier, previous health insurance information, salary, general biometric data, religious affiliation(s), previous religious affiliation(s), social media activity information, race, gender, previous gender, marital status, e-mail address(es), mobile phone number(s), wireline phone number(s), last four digits of social security number, MPI(s), NPI(s), bank or credit card information, credit information, ownership of real property, ownership of intellectual property, publications, indication of retail accounts, club memberships, past registration of sporting events, awards received, combinations thereof, or the like. The information that may be available on EHR(s) 140 may be used for the purposes of verifying and/or validating one's self-proclaimed identity.

In some cases, the resource system(s) 150 may be configured to verify a person's personal identity information, as provided by the person, to validate that person's claim of identity. In other cases, the HIRs 140 may be retrieved by the Independent Identity Authority System (170) and/or the Value Added Certificate Authorization System(s) 170 and used to validate a person's claim of identity. Further still, being able to access a particular HIR 140 from a resource system 150 associated with a user 102 who wishes to obtain a verified identity may be proof of the user's identity. In example embodiments, any combination of the aforementioned mechanisms may be used to verify a user's self-proclaimed identity.

The environment 100 may include value-added certificate authorization system(s) 160 that may be configured to cooperate with the client system 104 and other entities of the environment 100 to establish a CSI, register the CSI, bind the CSI with a set of HIRs contained within one or more Resource System(s) 150, bind a user's CSI to one or more CSIs created by one or more Healthcare Applications, and to set initial (and or to modify preexisting) permissions associated with a CSI. If a user tries to access resources, and/or has downloaded a healthcare application from the application download system 120 and/or the application store system 122, prior to establishing a registered CSI, then the user, via his or her client system 104, may be redirected to value-added certificate authorization system(s) 160 or otherwise instructed to create an initial CSI. In other cases, a user 102 may access value-added certificate authorization system(s), via their client system(s) 104 to establish their CSI. A user 102, via his or her client system 104, may access value-added certificate authorization system(s) 160 by any suitable manner, such as an HTTPS URL and or other web address.

Regardless of how a user 102, via his or her client system 104 arrives at the value-added certificate authorization system(s) 160, the value-added certificate authorization system(s) may interact with the client system 104 corresponding to the user 102, as well as independent identity system(s) 170 to establish the CSI for the user 102.

The environment 100 may include the independent identity system(s) 170 that may be configured to utilize a body of preexisting information to assist in verification of an identity of a user who attempts to establish a CSI. The independent identity system(s) 170 may be systems associated with organizations that already provide identity verification services, such as credit rating agencies and/or other individual rating or personal information tracking agencies. Some examples of such organizations may include EXPERIAN, TRANSUNION, EQUIFAX, U.S. SOCIAL SECURITY ADMINISTRATION, LEXIS/NEXIS, and/or the like.

When a user asserts a proposed CSI that is to be confirmed by value-added certificate authorization system(s) 160, the independent identity system(s) 170 may be configured to provide personal information about the user 102 to the value-added certificate authorization system(s) 160 for verification of the user's identity. In alternative embodiments, the resource system(s) 150, in addition to or instead of the independent identity system(s) 170, may be configured to interact with the value-added certificate authorization system(s) 160 to enable the value-added certificate authorization system(s) 160 to validate and/or verify personal identification information of a user 102. In these cases, the resource system(s) 150 may use existing medical records (e.g., HIRs 140), and the data contained thereon to verify personal identification information of a user 102. In many cases, the data contained on existing medical records may be relatively comprehensive, and therefore, may provide a mechanism for robust verification of identity.

In some cases, the value-added certificate authorization system(s) 160 may interact with more than one resource system(s) 150 to verify identity of the user 102. In other cases, a multi-source identity verification may be performed in conjunction with both independent identity system(s) 170, as well as one or more resource system(s) 150. This type of multi-source verification, whether with the resource system(s) 150 and/or the independent identity system(s) 170, may enhance the robustness of the verification, and in some cases, reduce or prevent errors in verification. One verification error may arise if a person should be validated based on the personal identity information that he or she provided, but is not (e.g., Type I error—null hypothesis of invalidation erroneously accepted). Another verification error may arise if a person should not be validated based on the personal identity information that he or she provided, but is validated (e.g., Type II error—null hypothesis of invalidation erroneously rejected). Multi-source verification may reduce or eliminate one or both types of errors that might occur in validating a person based on self-information provided by the person.

The environment 100 may include blockchain system(s) 180 that may be configured to maintain a healthcare blockchain to enable the functionality, as disclosed herein. It should be understood, therefore, that the blockchain system(s) 180 may be individual nodes that are configured to maintain the healthcare blockchain as a distributed ledger. Each of the nodes of the distributed ledger may be communicatively connected by any suitable mechanism, such as in a peer-to-peer protocol fashion, such as by the one or more network(s) 110. In some cases, the resource system(s) 150, as described above, may also be nodes in the distributed ledger of the healthcare blockchain. In this way, some resource system(s) 150 may also function as blockchain system(s) 180 and some blockchain system(s) 180 may also function as resource systems 150 and/or other system(s).

According to example embodiments, the blockchain system 180 may be configured to manage information distributed across various nodes, where each node may execute one or more algorithms to verify authenticity of elements to be added to the healthcare blockchain. Calculations and operations, as performed by the blockchain system(s) 180, as well as information received from other entities, may be journaled, as persistent storage, by hashing that information onto the healthcare blockchain via any suitable mechanism, such as Merkle Trees and/or other blockchain mechanisms. Such an approach may provide distribution of information that is incorruptible and immutable by other entities.

In example embodiments, the blockchain system(s) 180 may be configured to send and/or receive messages with other entities and/or applications operating on one or more other entities. These messages may be derived from the healthcare blockchain and/or are to be included to the healthcare blockchain. This communication may be via the one or more networks 110. In example embodiments, the blockchain system(s) 180 may receive an authorized CSI to be registered from value-added certificate authorization system(s) 160, such as when a user 102 establishes his or her authority to access the healthcare blockchain. The blockchain system(s) 180 may further receive newly established, and/or updated permissions to HIRs that are contained within EHRs 141, including PHI, from value-added certificate authorization system(s) 160.

The healthcare blockchain system(s) 180 may further be able to validate the integrity of a transaction that is to be included in the healthcare blockchain. In other words, the blockchain system(s) 180 may be configured to determine if an entity is authorized to add elements to the healthcare blockchain. This may entail the verification of a valid CSI associated with the transaction. Additionally, nodes (e.g., different blockchain system(s) 180) may cooperate to determine if another transaction (e.g., operating within a different network) should be added to the ongoing session. In other words, if during the course of an application (e.g., one involving the administration of a medication) another off-network application should be invoked (e.g., a medical reimbursement claim) smart contracts in the blockchain could interact with another blockchain network to affect side-chained interaction among multiple applications.

The blockchain system(s) 180 may also provide the processing bandwidth to both incorporate transactions onto the healthcare blockchain, maintain the healthcare blockchain, and/or generate and execute smart contracts as incorporated in the healthcare blockchain. For example, smart contracts incorporating the permissions, as set by a user 102, for access to his or her HIRs may be incorporated in the healthcare blockchain by the blockchain system(s) 180. Indeed, the blockchain system(s) 180 may also enable the execution of the conditions incorporated in the smart contracts, as incorporated in the healthcare blockchain. In example embodiments, the smart contracts may adjudicate the issuance of access tokens, such OAuth2 tokens that enable access to HIRs, as stored at resource system(s) 150.

There may be a variety of mechanisms for adding a distributed ledger node to the healthcare blockchain. It should be noted that the blockchain systems 180 may be of a permissioned variety (e.g., it may comprise only pre-sanctioned peer nodes) or non-permissioned variety. For the permissioned type, there may be a mechanism by which new prospective peer nodes are to be approved via a governance process prior to the new node being added to conduct transactions on the healthcare blockchain. This may entail a variety of methods, such as voting among peer nodes to determine which candidates should be admitted into the healthcare blockchain.

Figure 2:
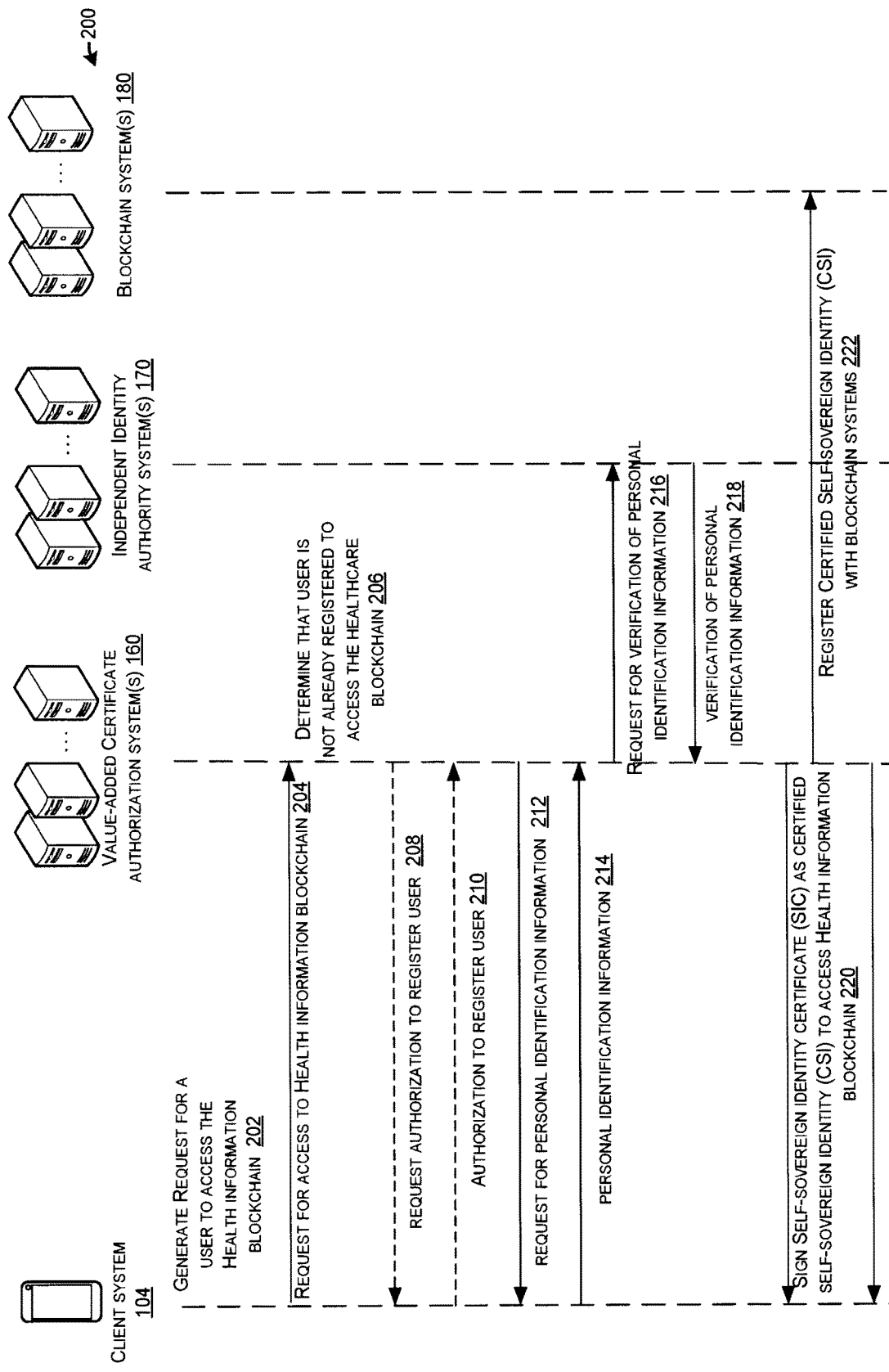
FIG. 2 is a chart illustrating example operations for registering a client system with a certified self-sovereign identity access a healthcare blockchain, according to example embodiments of the disclosure.

FIG. 2 is a chart illustrating example operations 200 for registering a client system 104 with a certified self-sovereign identity access a healthcare blockchain, according to example embodiments of the disclosure. In example embodiments, the operations 200 may be non-recurring, and may only be performed once for each user and once for each healthcare application for whom access to the healthcare blockchain is to be provided. These operations 200, in example embodiments, may be performed by interactions between a client system 104, value-added certificate authorization system(s) 160, independent identity system(s) 170, and blockchain system(s) 180. In example embodiments, other entities of environment 100 may be included in the performance of operations 200.

The execution of the operations 200 and interactions thereof may result in the certification, signing, and/or registration of a certified self-sovereign identity (CSI). The CSI may be any suitable certificate (e.g., x.509 compliant) to enable access by a client system 104 and associated user 102 to the healthcare blockchain, such as those enabled by public-private key pairs (e.g., PKI, PKIx, etc), hashed (e.g., MD5, SHA 256, etc) enabled digital signatures and other cryptographic methods. A private CSI key may be stored on the client system 104 and a corresponding public CSI key may be registered with the healthcare blockchain and/or value-added certificate authorization system(s) 160. The registration of the CSI key and/or incorporation of the CSI key into the healthcare blockchain may grant healthcare blockchain access rights to the user 102 for whom the CSI is established and/or registered.

In example embodiments, only one registered CSI may be established for a particular user 102. However, the particular user 102 may create additional CSI or each healthcare application installed on their client system 104 and/or more than one client system 104 to access HIRs and/or manage permissions to HIRs. In the illustrated embodiment, for example, operations 200 of FIG. 2 apply for only a user 102 who does not already have access to the healthcare blockchain. In this example, the operations 200 may be performed only once for each user's client system 104, to access the healthcare blockchain, as managed by the blockchain system(s) 180. If a user 102 attempts to establish a second CSI for a particular client system 104, then that user 102 may be prevented from proceeding, such as by the mechanism discussed below in conjunction with FIG. 3.

In example embodiments, a particular client system 104 may create a CSI and a CSI key pair which will be unique with the public portion of a private-public key pair incorporated into the healthcare blockchain and certificate authority. Furthermore, the private CSI key may be stored on the client system 104 associated with the user 102. In further example embodiments, the registered CSI may be bound or identified with other preexisting user identifiers, such as a virtual unique patient identifier (UPI), a Medical Record Number (MRN) identifier, a Master Patient Index (MPI), or the like. In this way, other preexisting mechanisms for identifying a particular user may be incorporated within the CSI to enable integrated access to those HIRs, even if those resources are legacy resources that do not completely comply with the standardizations and mechanisms disclosed herein.

The operations 200 may include, at 202, the client system generating a request to access the blockchain. The request to access the blockchain may alternatively by considered a request to certify a self-sovereign identity that one may use via his or her client system 104 to access the blockchain. In some example embodiments, the request may be generated by interacting with a web interface of a value-added certificate authorization system(s) 160 and/or by any other mechanism for interacting with value-added certificate authorization system(s) 160. In other example embodiments, the request may be generated locally on the client system 104 by execution one or more instructions of a software or application operating thereon. Regardless of the mechanism of generating the request, the request may include information such as information about the user (e.g., name, DOB, etc.) of the user for whom the CSI is to be registered.

At 204 the request may be sent to the value-added certificate authorization system(s) 160, such as via the networks 110. In example embodiments, where the request is generated by interfacing with a web interface of the value-added certificate authorization system(s) 160, the processes 202 and 204 may be executed substantially concurrently and in an integrated fashion. In some cases, a user 102 as interacting with his or her client system 104 may be redirected to the value-added certificate authorization system(s) 160 to establish access to the healthcare blockchain by another entity, such as the application download system(s) 120.

At 206, value-added certificate authorization system(s) 160 may determine and/or verify that the user 102 is not already registered to access to the healthcare blockchain. In other words, process 206 may prevent the registration of multiple CSIs to a single user 102 and/or it may initiate a new user registration process of operation 208. The case where a requesting user already has an established CSI key is discussed below in conjunction with FIG. 3.

At 208, value-added certificate authorization system(s) 160 may permit and determine to request authorization to register the user 102. This may entail the user 102, via his or her client systems 104, acknowledging one or more stipulations and/or agreeing to adhere to rules and/or regulations associated with the mechanism of managing and providing HIR as disclosed herein. At block 210, authorization to register the user may be provided by the client system 104 to the value-added certificate authorization system(s) 160. This authorization may be responsive to the request for the authorization at 208. In some example embodiments, the operations of 208 and 210 may be optional, as the initial request for access to the healthcare blockchain at 206 may serve as authorization to register the user 102.

At 212, the value-added certificate authorization system(s) 160 may request one or more personal identification information elements from the user 102 via his or her client system 104. The personal identification information may be any type of information that may be used to establish and/or verify the identity of the user 102 requesting access to the healthcare blockchain. This personal identification information of the user 102, as requested, may include, but is not limited to, name, date of birth, present address, old address(es), e-mail address(es), mobile phone number(s), wireline phone number(s), last four digits of social security number, MRM numbers, MPI(s), NPI(s), bank or credit card information, credit information, insurance information, ownership of real property, ownership of intellectual property, publications, indication of social media accounts, indication of retail accounts, club memberships, past registration of sporting events, awards received, social security number, combinations thereof, or the like. The value-added certificate authorization system(s) 160 may also request information about the user's healthcare provider (e.g., identity of his or her healthcare provider) which may be used to interface to other provider identification systems (e.g., NPIs).

At 214, the personal identification information may be provided by the client system 104 to the value-added certificate authorization system(s) 160. This personal identification information may be provided responsive to the request at 212. The personal identification information, as provided by the client system 104 to the value-added certificate authorization system(s) 160 may be entered and/or provided to the client system 104 by the user 102 for whom access to the healthcare blockchain is to be established. This personal identification information, as provided by the user 102, on his or her client system 104 and provided to the value-added certificate authorization system(s) 160 may include, but is not limited to, name, date of birth, previous names, addresses, previous addresses, social security number, patient identifiers, unique patient identifiers, medical record numbers (MRNs), emergency contacts, parent's names, mother's maiden name, children's names, spouse's name, previous spouse(s) identifiers, driver's license number, previous driver's license information, passport number, citizenship information, previous citizenship(s), foreign nation(s) visited, current employer(s), previous employer(s), current educational institution(s) of affiliation, previous educational institution(s) attended, educational degree(s) granted, licenses and/or certificates granted, credit score, health insurance carrier, previous health insurance information, salary, general biometric data, religious affiliation(s), previous religious affiliation(s), social media activity information, race, gender, previous gender, marital status, e-mail address(es), mobile phone number(s), wireline phone number(s), last four digits of social security number, MPI(s), NPI(s), bank or credit card information, credit information, ownership of real property, ownership of intellectual property, publications, indication of retail accounts, club memberships, past registration of sporting events, awards received, combinations thereof, or the like. In some cases, the categories of the personal identification information may include information that may be found on a user's EHR(s) 140.

At 216, the value-added certificate authorization system(s) 160 may request the verification of the personal identification information by the independent identity authority system(s) 170. The independent identity authority system(s) 170, as discussed above, may be repositories of personal information for a relatively large number of people. For example, the independent identity authority system(s) 170 in the form of a credit rating agency may have a variety of information about an individual's financial, credit, name change, address, employment status and or other histories. Thus, the independent identity authority system(s) 170 may be able to use the personal identification information, as provided by the user 102 via his or her client system 104, to determine if the user 102 is indeed who he or she says he or she is.

It should be noted that in some example embodiments, the value-added certificate authorization system(s) 160 may request the verification of the personal identification information from one or more resource system(s) 150 instead of, or in addition to, one or more independent identity authority system(s) 170. The resource system(s) 150 may be configured to verify the personal identification information, by using the information that may be available on protected documents, such as the EHR(s) 140. Thus, the resource system(s) 150 may compare the personal identification information as provided by a user 102 to the value-added certificate authorization system(s) 160 to information that the resource system(s) 150 may have access to independently, such as on one or more EHRs 140. The resource system(s) 150, like the independent identity system(s) 170, may use any variety of criteria for determining if the personal identification information is valid, such as correlation of a predetermined number and/or percentage of user provided personal identification information elements.

At 218, the independent identity authority system(s) 170 may verify and indicate a verification of the user 102 and/or his or her CSI to the value-added certificate authorization system(s) 160. If the personal identification information could not be verified by the independent identity authority system(s) 170, then registration of the user for access to the healthcare blockchain may cease and value-added certificate authorization system(s) 160 may notify the user 102 of the same, such as via his or her client system 104. However, if the user 102 is verified based at least in part on the personal identification information, as provided, then the independent identity authority system(s) 170 may indicate to value-added certificate authorization system(s) 160 of the positive verification of personal identification information. As discussed above, in some cases, the verification information may be generated and/or sent to the value-added certificate authorization system(s) 160 from the resource system(s) 150 rather than the independent identity system(s) 170.

It should be understood that this verification process may involve the value-added certificate authorization system(s) 160 sending the personal identification information it receives from the client system 104 to the independent identity authority system(s) 170 for verification. For example, the value-added certificate authorization system(s) 160 may package the user's personal identification information into a package and send the same, such as via the one or more network(s) 110 to the independent identity authority system(s) 170 for verification. At that point, the independent identity authority system(s) 170 may access a body of personal information associated with the user 102 who is to be certified, as available to the independent identity authority system(s) 170. This body of personal information about the user 102 is independently obtained, in many cases over a relatively long period of time, from the personal identification information, as provided by the value-added certificate authorization system(s) 160.

The independent authority system(s) 170 may compare information elements in the body of personal information about the user 102 to corresponding elements in the personal identification information of the user 102, as received from value-added certificate authorization system(s) 160. The determination of verification may be based at least in part on this comparison. The comparison may result in a percentage match between corresponding data elements of the personal identification information and the independent body of information about the user 102. This percentage match may be compared to a threshold level to determine verification of the personal identification information. For example, if the match is greater than 90%, it may be determined that the personal identification information is verified. In some cases, the determination of the match may be weighted, where certain data elements of the personal identification information may carry greater weight than others. For example, a personal identification information element of an old address may have less weight than a change of name. As a result, if a user 102 forgets an old address, something that is easy to forget, then that may not affect him or her as adversely as forgetting his or her name change, which is an event that is less likely to be forgotten by an individual.

As an alternative to the independent identity authority system(s) 170 verifying the personal identification information, according to example embodiments, the value-added certificate authorization system(s) 160 may receive the independent personal information about the user 102 from the independent identity authority system(s) 170 and perform the verification. In other words, the value-added certificate authorization system(s) 160 may request and/or obtain the independent identity information from the independent identity authority system(s) 170 and compare that information with the personal identification information, as received from the client system 104 to verify the user 102 for whom access to the healthcare blockchain is requested.

As another alternative, the value-added certificate authorization system(s) 160 may request verification 216 from a number (e.g., two) of separate entities that are configured to provide verification of the personal identity information, such as one or more independent identity authority system(s) 170 and/or one or more resource system(s) 150. The value-added certificate authorization system(s) 160 may employ any suitable mechanism to adjudicate a verification of the personal identification information in a multi-source scheme, such as all verifying entities 150, 170 must return an indication of verified, or a majority of the verifying entities 150, 170 must return an indication of verified.

At 220, responsive to verification of the personal identification information of the user and the construction of a self-sovereign identity certificate (SIC), value-added certificate authorization system(s) 160 may sign the SIC, thus creating a certified self-sovereign identity (CSI). The CSI may comply with the x.509 CA standard and as such may comprise an intermediate certificate authority, such as one operating in conjunction with a standard root certificate authority found in mobile and desktop web browsers. Both the intermediate and the root CA may be chained in accordance with a certified path validation processes (e.g. RFC 5280) and/or employ common public key methods (e.g., PKIX). The act of signing the SIC may establish and/or certify the CSI to enable, for the user 102, via his or her client system 104, to access the healthcare blockchain. Established CSIs may incorporate key pairs (e.g., unique public and private, keys operating isochronously on both client and server systems, etc.) for accessing the healthcare blockchain. In this case, value-added certificate authorization system(s) 160 may digitally sign the SIC of the user 102 to register the CSI's public key. The CSI key pair may include a private CSI key that may be stored on the client system 104 associated with the user 102 to whom the CSI key belongs. In some cases, upon initiation of a session between a client system 104 and various other systems, a disposable symmetric key may be generated to secure subsequent information transfers.

At 222, value-added certificate authorization system(s)) 160 may register the CSI with the blockchain system(s) 180. The CSI public key and other CSI certificate information may be registered with and/or hashed as a transaction onto the healthcare blockchain. The CSI is to be used subsequently by the client system 104 and the user 102 thereon to access the HIRs to which the user 102 may be entitled to access.

At 224, value-added certificate authorization system(s) 160 may instruct redirection to the application operating in the client system. For example, once the CSI has been signed and further registered with the blockchain system(s) 180, the client system 104 may be ready to download one or more healthcare applications of the user's choosing, and bind those one or more healthcare applications to the user's CSI, as established by the operations 200. Thus, this redirection may be to an application download system 120 and/or an application store system 122 and or to other client system applications.

Figure 3:
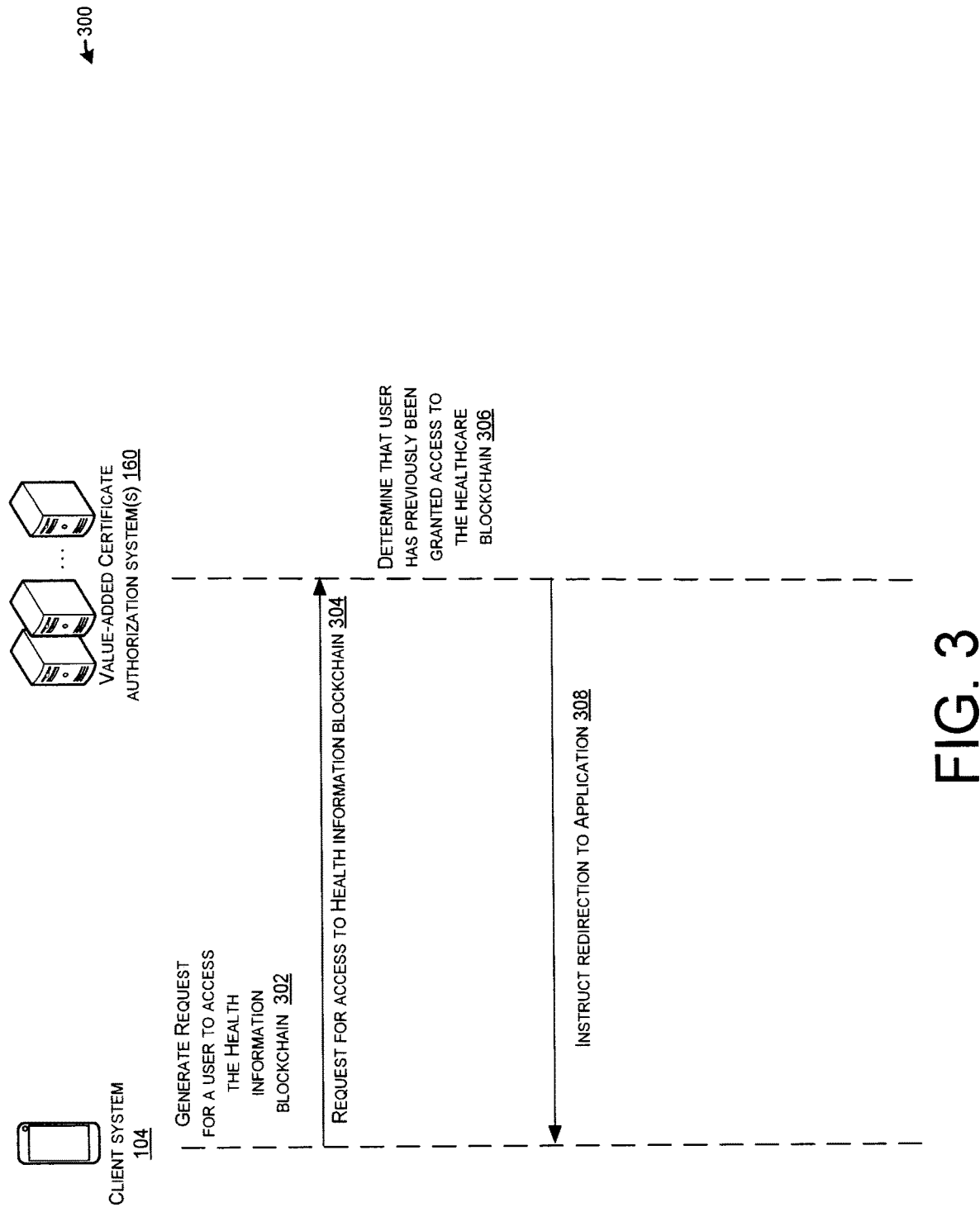
FIG. 3 is a chart illustrating example operations for redirecting a client system to obtain a healthcare application if the client system attempts to register a user who is already registered, according to example embodiments of the disclosure.

FIG. 3 is a chart illustrating example operations 300 for redirecting a client system 104 to obtain a healthcare application if the client system 104 attempts to register a user who is already registered to access the healthcare blockchain, according to example embodiments of the disclosure. When a user 102 who is already registered (e.g., the user 102 has established a CSI) attempts to register again, or in other words, establish a second CSI, value-added certificate authorization system(s) 160 may disallow redundant CSIs for a single user 102. These operations 300, in example embodiments, may be performed by interactions between a client system 104 and value-added certificate authorization system(s) 160. In example embodiments, other entities of environment 100 may be included in the performance of operations 300.

At 302, a client system 104 may generate a request for a user to access the HIR blockchain. This operation may be similar to operation 202 of FIG. 2, and in the interest of brevity, the description of the same will not be repeated here.

At 304, the request for access to the blockchain may be sent to the value-added certificate authorization system(s) 160. This transmission may be via the network(s) 110 or any other suitable mechanism for sending the request for access to the blockchain.

At 306, the value-added certificate authorization system(s) 160 may receive the request and make a determination that the user has previously been granted access to the healthcare blockchain. In other words, the value-added certificate authorization system(s) 160 had previously registered and signed the user's CSI, and using that previously registered CSI, the user already has access to the healthcare blockchain. To make this determination, value-added certificate authorization system(s) 160 may be configured to compare the user's pseudonymous identity with a list of registered CSI keys stored in a database that have been issued to users 102. Alternatively, the registration of the user 102 may be determined, in cooperation with the blockchain system(s) 180, by identifying his or her registered CSI at the healthcare blockchain. From this comparison, and by identifying a preexisting registered CSI associated with the requesting user 102, it may be determined by the value-added certificate authorization system(s) 160 that the user 102 has already been granted access to the healthcare blockchain.

At 308, value-added certificate authorization system(s) 160 may instruct a redirection of the client system 104 to an application download system 120. This redirection of the client system 104 may be responsive to value-added certificate authorization system(s) 160 determining that the access requesting user already has access to the healthcare blockchain.

In some alternate example embodiments, the value-added certificate authorization system(s) 160 may notify the user 102 via his or her client system 104 that he or she is already registered to access the healthcare blockchain. In further example embodiments, the value-added certificate authorization system(s) 160 may notify the user 102, via his or her client system 104, of the CSI that already exists for the user 102. In still further example embodiments, the value-added certificate authorization system(s) 160 may redirect the user 102 to retrieve his or her CSI on a new client device 104 as outlined below.

The blockchain system may incorporate multi-signature file access capabilities wherein an encrypted file containing a user's full CSI and current client healthcare application access credentials may be uploaded to the blockchain. If a CSI is lost, or a user wishes to change his or her client device 104 (e.g., get a new smartphone), the value-added certificate authorization system(s) 160 may assist in the recovery of the user's preexisting CSI. In this case, the value-added certificate authorization system(s) 160 may co-sign with the client system 104 as its trusted witness, and the original encrypted CSI file may then be downloaded to the new client system 104 directly from the blockchain system(s) 180 and installed on the new client system 104. A similar arrangement could be used to register and bind additional client system(s) 104 to a single CSI.

Figure 4:
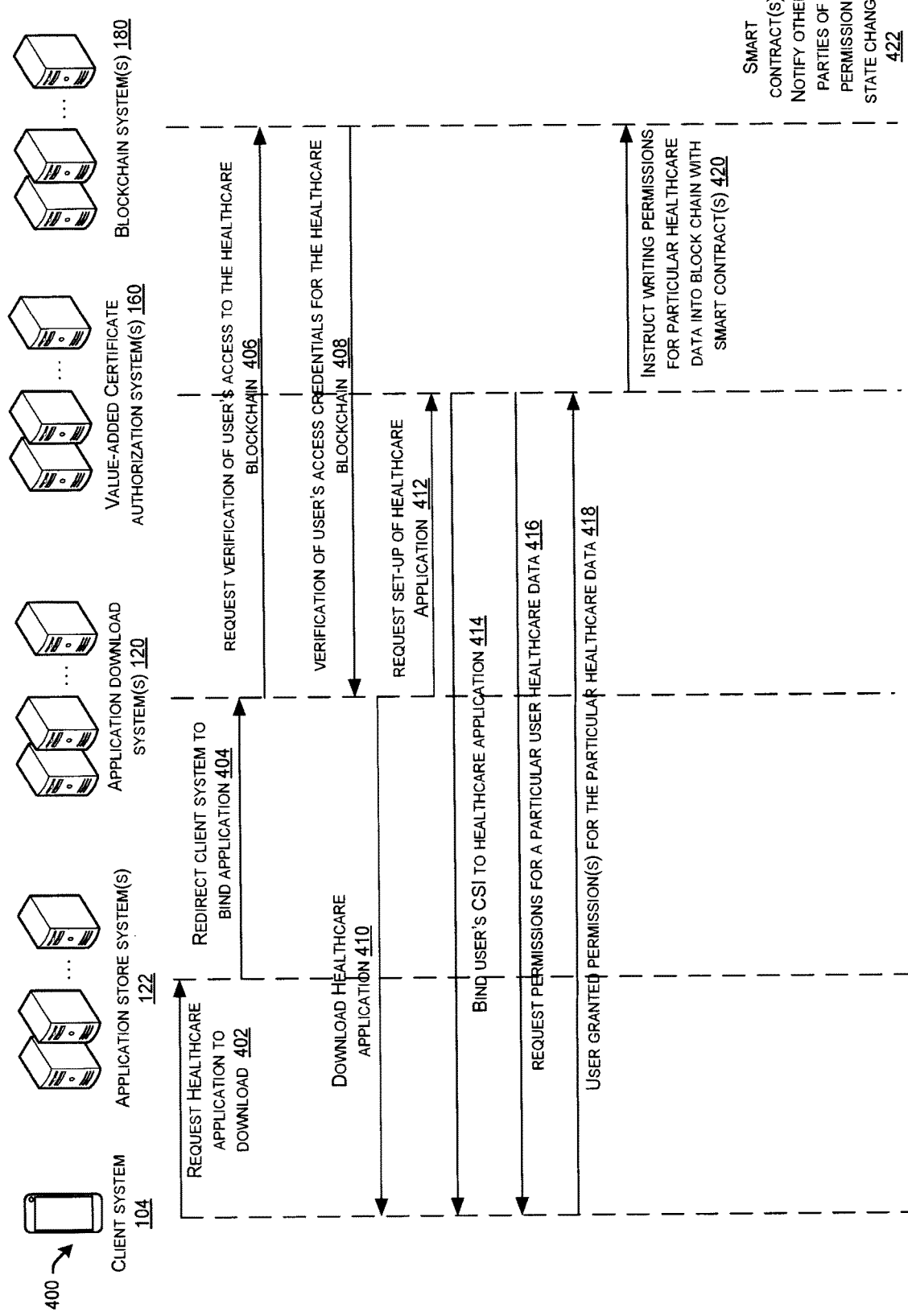
FIG. 4 is a chart illustrating example operations for setting up a healthcare application for and use in setting user permissions and to authorize access to health information resource(s), according to example embodiments of the disclosure.

FIG. 4 is a chart illustrating example operations for setting up a healthcare application for and use in setting user permissions and to authorize access to health information resource(s), according to example embodiments of the disclosure. It will be appreciated that these operations 400 may be performed when a new healthcare application is to be bound with the user's CSI on his or her client system 104. These operations 400, in example embodiments, may be performed by interactions between a client system 104, application store system(s) 122, application download system(s) 120, value-added certificate authorization system(s)) 160, and blockchain system(s) 180. In example embodiments, other entities of environment 100 may be included in the performance of operations 400.

At 402, a client system 104 may request download of a healthcare application. This request may be to the application store system(s) 122 or directly to the application download system(s) 120. If the request is to the application store system(s) 122, then, at 404, the client system 104 may be redirected to the application download system(s) 120 to bind the healthcare application to the user's CSI.

At 406, the application download system(s) 120 may request verification of the user's access to the healthcare blockchain. The blockchain system(s) 180 by way of a smart contract may be configured to provide the verification of the user's access to the healthcare blockchain.

At 408, smart contracts in the healthcare blockchain, as executed by the blockchain system(s) 180, may verify the user's access to the healthcare blockchain. The smart contract(s) associated with the user's CSI may generate a verification message that is sent to the application download system(s) 120 to indicate that the user 102 is allowed to access the blockchain system(s) 180 with a registered CSI. In other words, the user 102 had previously engaged, via the client system 104, in the operations 200 of FIG. 2.

At 410, responsive to verifying the user's access to the healthcare blockchain, the requested healthcare application may be downloaded to the client system 104. As the healthcare application is downloaded, a digital wallet on the client device 104 may also be configured by smart contracts in the healthcare blockchain.

At block 412, while or after the healthcare application is downloaded to the client system 104, the application download system(s) 120 may request value-added certificate authorization system(s) 160 to set-up of the healthcare application, as downloaded and installed on the client system 104.

At 414, value-added certificate authorization system(s) 160 may bind the user's CSI to the healthcare application. This may involve handing off, identifying, and/or instructing the storing of the CSI in a storage location of the client system 104 where the healthcare application may access the CSI for managing permissions and HIRs.

After binding the CSI to the healthcare application on the client system 104, the value-added certificate authorization system(s) 160 may assist the user 102, via his or her client system 104 with the healthcare application operating thereon, to establish permissions to his or her HIRs by the operations 416, 418, 420, and 422. At 416, the value-added certificate authorization system(s) 160 may request permissions for the application to access particular user healthcare data resources 416. This particular healthcare data may reside in an EHR stored at a resource system 150 of the user's healthcare provider 102.

At 418, the user may indicate permission(s) for the application to access particular healthcare data resources. The permission(s) may include permission for a single entity (e.g., patient's doctor), or multiple entities (e.g., patient's doctor, patient's pharmacy, patient's health insurance company, and patient's mother). In some cases, the permission(s) as granted by the user 102 may indicate conditional permissions, where the user 102 may specific one or more stipulations under which a party may gain access to the particular healthcare data.

At 420, the value-added certificate authorization system(s) 160 may instruct writing permissions for the particular healthcare data into smart contract(s) contained in the healthcare blockchain. In other words, smart contract(s) may be included in the healthcare blockchain the execution of which allows access to the particular healthcare data in accordance with the permissions established by the user 102.

At 422, the smart contract(s), the logic of which are executed by the blockchain system(s) 180, may notify other entities of the change or permissions in the healthcare blockchain. This may, in some example embodiments, be performed according to representational state transfer (REST) protocols and/or incidental to the normal operations of peer node in the blockchain system itself. The notification of permission state change may be sent to one or more client system(s) 104 associated with a user(s) 102 who may be granted permissions to the particular healthcare data. Additionally, the permission state change may be communicated to the value-added certificate authorization system(s) 160. Further still, the permission state change may be sent to resource system(s) 150, in the case where the resource system(s) 150 are separate entities from the blockchain system(s) 180.

Figure 5:
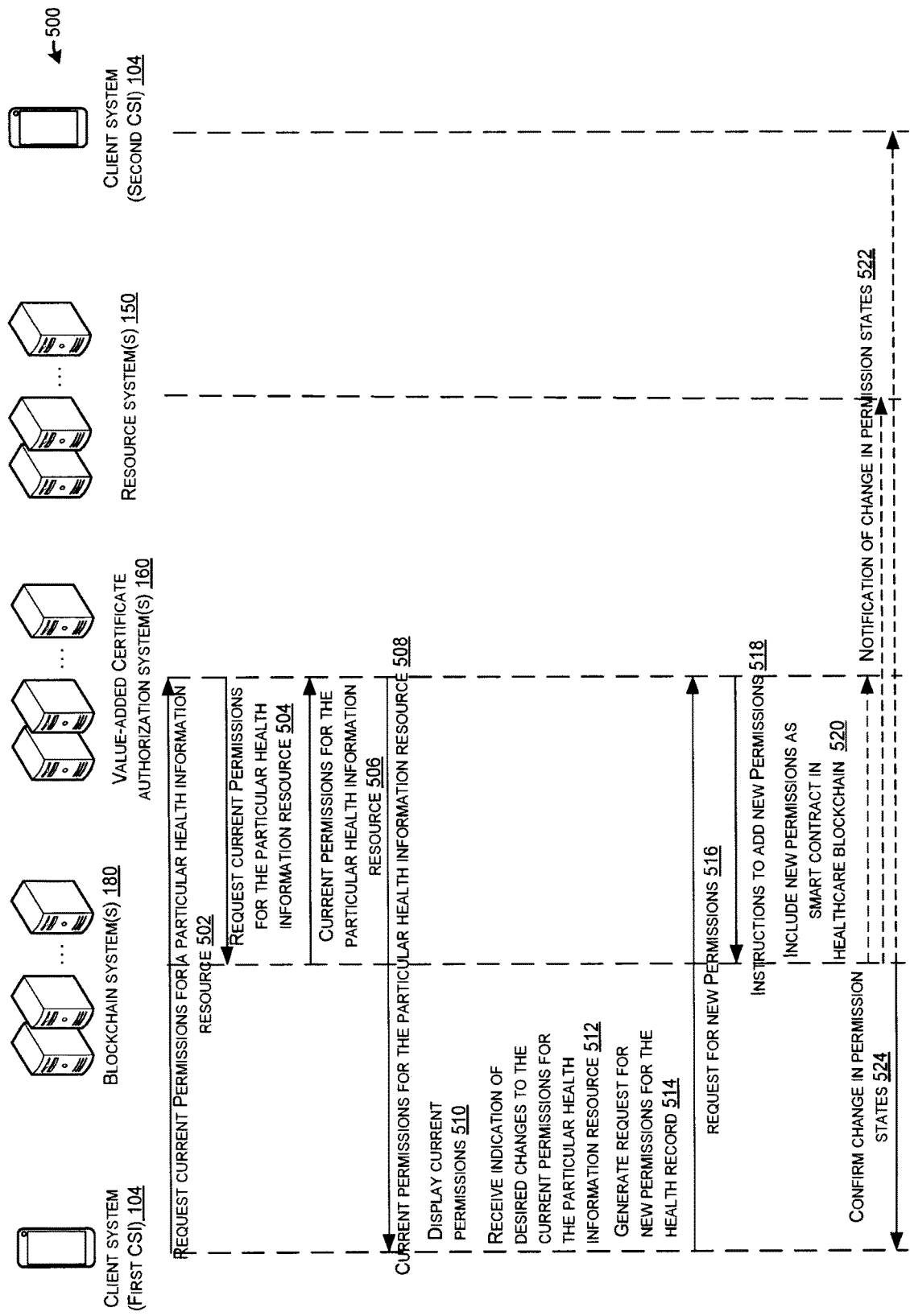
FIG. 5 is a chart illustrating example operations for setting up a healthcare application for use in updating and/or setting user permissions after initial permission grants, according to example embodiments of the disclosure.

FIG. 5 is a chart illustrating example operations 500 for setting up a healthcare application for use in updating and/or setting user permissions after setting up the healthcare application, according to example embodiments of the disclosure. These operations 500 may be performed every time a user 102 wishes to establish and/or modify permissions associated with his or her HIRs.

At 502, current permissions for a particular HIR may be requested by a first client system 104. This request may be sent to the value-added certificate authorization system(s) 160. The value-added certificate authorization system(s) 160 may then at 504 request the current permissions for the health information resource from the healthcare blockchain system(s) 180 to determine the permissions associated with the particular HIR. At 506 the smart contracts in the blockchain associated with the particular resource may generate a file indicating the current permissions of the particular resources associated with a given application. The current permissions for the particular health information resource may be sent to the value-added certificate authorization system(s) 160. Next, the value-added certificate authorization system(s) 160, at 508, may send the current permissions for the particular health information resource to the first client system 104.

At 510, the first client device 104 may then display the current permissions and conditions associated with a particular application. As discussed herein, the permissions associated with the particular application may include conditional resource access permissions. For example, the conditions may show that the user's brother may have access to the HIRs for the next 30 days, or a researcher may have access to the heath resource if it is anonymized. In example embodiments, such conditions and/or stipulations of the permissions of the particular HIR may be displayed to the user 102 on a display of the first client system 104.

At 512, the first client device 104 may receive indications of desired changes to the current permissions of the particular HIRs. These changes may be entered by a user 102 who has rights to change the permissions for the particular HIR, such as a patient for whom the HIR pertains, on the first client system 104. For example, the new desired permissions and/or changes to the permissions may be entered on any suitable user interface of the first client system 104, such as a graphical interface on a touch screen of the first client system 104.

At 514, the first client device 104 may generate a request for new permissions for the HIR. This request may indicate all of the changes to the current permissions, as requested by the user 102 at 508. The new permission requests and/or changes to the current permissions for the particular HIR may be coded in one or more messages. At 512, the first client device may send the request via one or more networks 110 for new permissions to the value-added certificate authorization system(s) 160.

At 518, the value-added certificate authorization system(s) 160 may instruct the blockchain system(s) 180 to add the new permissions for the particular HIR. This process may entail determining that the user 102, having his or her CSI and associated with the first client system 104, is authorized to modify the permissions for the particular HIR. This verification may be performed locally at the certificate verification system(s) 160, or alternatively, may be performed by query to the blockchain system(s) 180 or by invoking a smart contract resident within the blockchain system 180. The value-added certificate authorization system(s) 160, according to some example embodiments, may instruct the blockchain system(s) 180 only after verifying the identity and permissions of the requesting users using his or her CSI, as received from the first client system 104.

At 520, new permissions may be added to the healthcare blockchain as a smart contract. The smart contract may be generated at the blockchain system(s) 180, in accordance with the requested permissions as instructed in 514. The smart contract, as incorporated in the blockchain at this operation 516, may be configured to issue access token(s) (e.g., OAuth2 tokens) to permissioned users 102 of the particular HIR, subject the permissions conditions stipulated with the modified permissions. It should be noted that older permissions may remain as part of the healthcare blockchain. However, updated permissions, or in other words, it is appreciated that an aspect of normal blockchain operations provides that the most temporally recent permissions associated with a HIR will control the access thereto. Moreover, another feature of private, or permissioned, blockchains of the sort to used in the healthcare blockchain system is the ability for the consensus participating nodes to direct a hard fork—i.e., a new version of the blockchain correcting errors in code and or data contained therein.

At 522, there may be a variety of notifications of permission states that are sent to other entities that may be affected by the changes in the permissions for the particular HIR. For example, the value-added certificate authorization system(s) 160 may be sent a confirmation of the changes. In some cases, the value-added certificate authorization system(s) 160 may maintain an independent registry of permissions, at least for a limited period of time. The block chain system(s) 180 may optionally notify one or more resource system(s) 150 where the particular HIR resides, unless those resource system(s) 150 are nodes of the blockchain, or in other words, are also blockchain system(s) 180 themselves. One or more other client system(s) 104 may also be notified. For example, if permissions are extended, revoked, and/or conditions modified, for a second CSI, and the user 102 associated with that CSI, then the client system 104 associated with that CSI, and the healthcare applications operating thereon, may be notified of any permission changes pertaining to the second CSI. It is also appreciated that any and all systems operating as full peer nodes on the blockchain always have near real time information on any and all state changes occurring in the network thus rendering the need for further notifications moot.

At 520, a confirmation of the change in permissions state may be sent to the first client system 104. Thus, the user 102 may receive confirmation of the changes that he or she wished to implement for his or her particular HIR.

Figure 6:
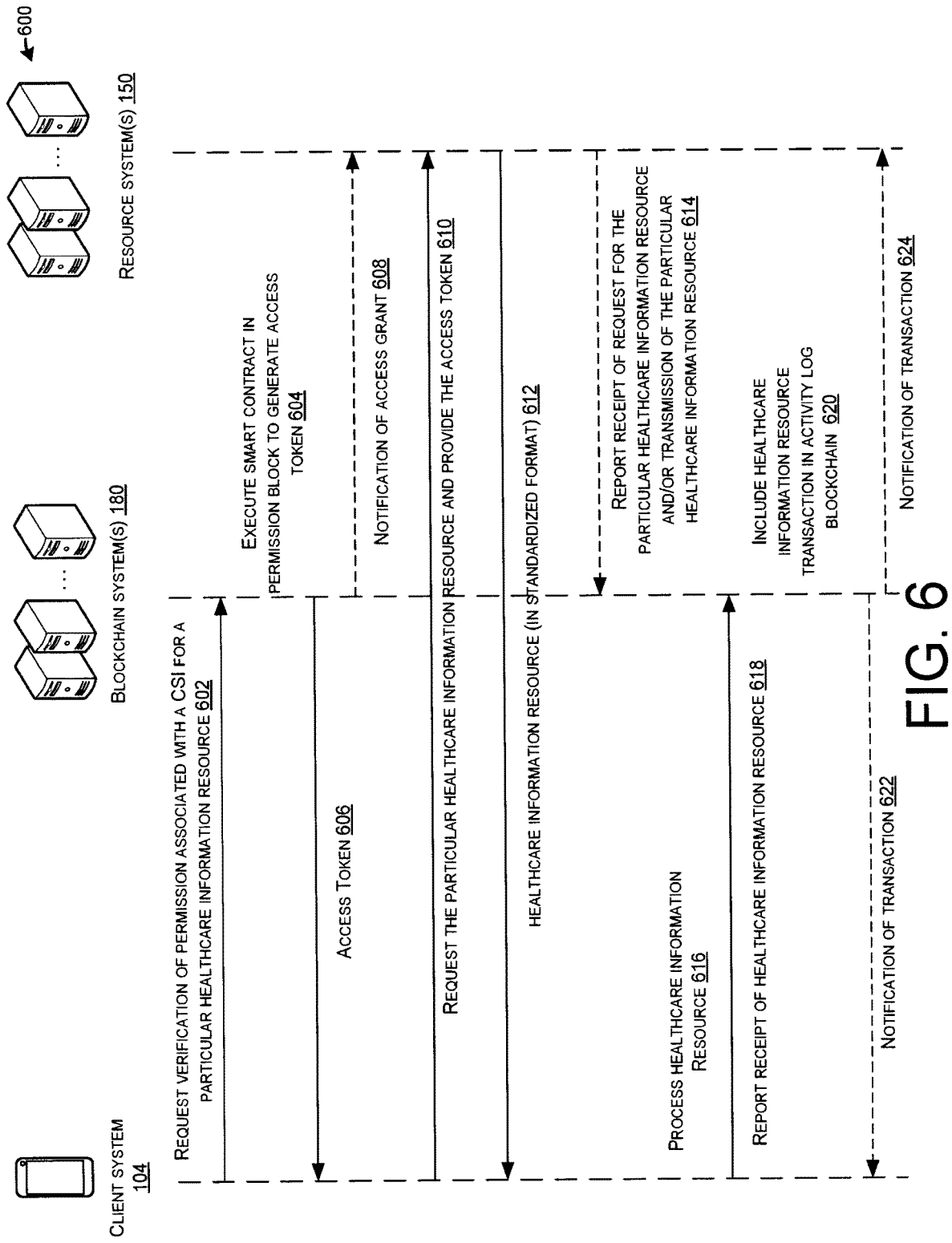
FIG. 6 is a chart illustrating example operations for a client system to access health information resource(s), according to example embodiments of the disclosure.

FIG. 6 is a chart illustrating example operations 600 for a registered and permissioned user to access HIRs, according to example embodiments of the disclosure. The operations 600 may be performed every time that a client system 104 may attempt to acquire HIRs on behalf of a user 102. These operations 600, in example embodiments, may be performed by interactions between a client system 104, and blockchain system(s) 180, and the resource system(s) 150. In example embodiments, other entities of environment 100 may be included in the performance of operations 600.

At 602, the client system may request verification of permission associated with a CSI for a particular health information resource. The CSI, in this case, may be the CSI of the user 102 of the client device 104. The request for verification of permission may pertain to a particular healthcare data (e.g., EHR, PHI, etc.) and may be referenced in the request, such as by a unique identifier of the healthcare data resource.

At 604, responsive to receiving the request for verification of permissions associated with the CSI, the blockchain system(s) 180 may execute the smart contract associated with the healthcare data of the request and the CSI of the request. If the particular healthcare data has more than one permission pertaining to specific resource for the CSI to a specific application, then the most recent permission, and the smart contract(s) therein, may control access. If the CSI of the request is indeed authorized, then the execution of the smart contract may result in the issuance of an access token for the healthcare data and the CSI of the request. The access token may be of any suitable format, such as OAuth2 standards. At 606, the access token may be sent to the client device 104 by the blockchain system(s) 180, such as via the one or more network(s) 110.

At 608, the blockchain system(s) 180 may notify resource system(s) 150 where the particular healthcare data of the request may reside. This operation 608 may be optional, particularly in cases where the resource system(s) 150 and the blockchain system(s) 180 are coincident with one another.

At 610, the client system may generate a request for the particular HIR to be sent to the resource system(s) 150. This request may be sent along with the access token, as received by the client system 104 at 606. The request for the HIR may include a unique identifier of the HIR and be formatted in standard web services language (e.g., XML, JWT, etc) and in conformance with the resource systems authentication and authorization protocols (e.g., TLS, OAuth2, etc).

At 612, responsive to receiving the request for an HIR, the resource system(s) 150 may provide the HIR, such as in a standardized format, to the client system 104. The resource system(s) 150 may verify the authenticity of the access token prior to providing the HIR. In other cases, the resource system(s) 150 may use the notification, as received from the blockchain system(s) 180 at 608 as a mechanism to validate the request for the HIR, as received from the client system 104 at 610. In some example embodiments, the disbursement of the HIR by the resource system(s) 150 may be gated by both the verification of the access token received from the client system 104 and independent notification of access received from the blockchain system(s) 180. In other embodiments, the resource system 150 may operate as a peer node in the blockchain network rendering the need for further notifications moot.

The standardization by which the requested HIR is provided may be a result of an API at the front end of the resource system(s) 150. In some cases, the standardization of the data format may result in highly granular data with standardized labeling of the data. It will be appreciated that this type of standardization of how the healthcare data is disbursed, may spawn a number of different healthcare applications, resulting in greater innovation and customization of healthcare applications available to users 102 and other entities 102.

At 614, the client system may process the HIR. This may entail arranging the HIR, storing the HIR, further analyzing the HIR, and/or displaying the HIR, such as on a display of the client system 104.

At 616, the client system 104 may report receiving the requested HIRs. At 618, the healthcare transaction of the client system 104 receiving the requested HIRs may be recorded in an activity log blockchain. A de-facto activity log may be derived from the healthcare blockchain where the permissions and provenance associated with HIRs consumed pursuant to operations 600 within the network are immutably recorded.

At 620, the blockchain system(s) 180 may optionally notify the client systems' digital wallets 104 of the update of recording the HIR transaction. Similarly, at 622, the blockchain system(s) 180 may optionally notify the resource system(s) 150 of the update of recording the HIR transaction. In other embodiments, the resource system may operate as a peer node in the blockchain network rendering the need for further notifications moot.

Figure 7:
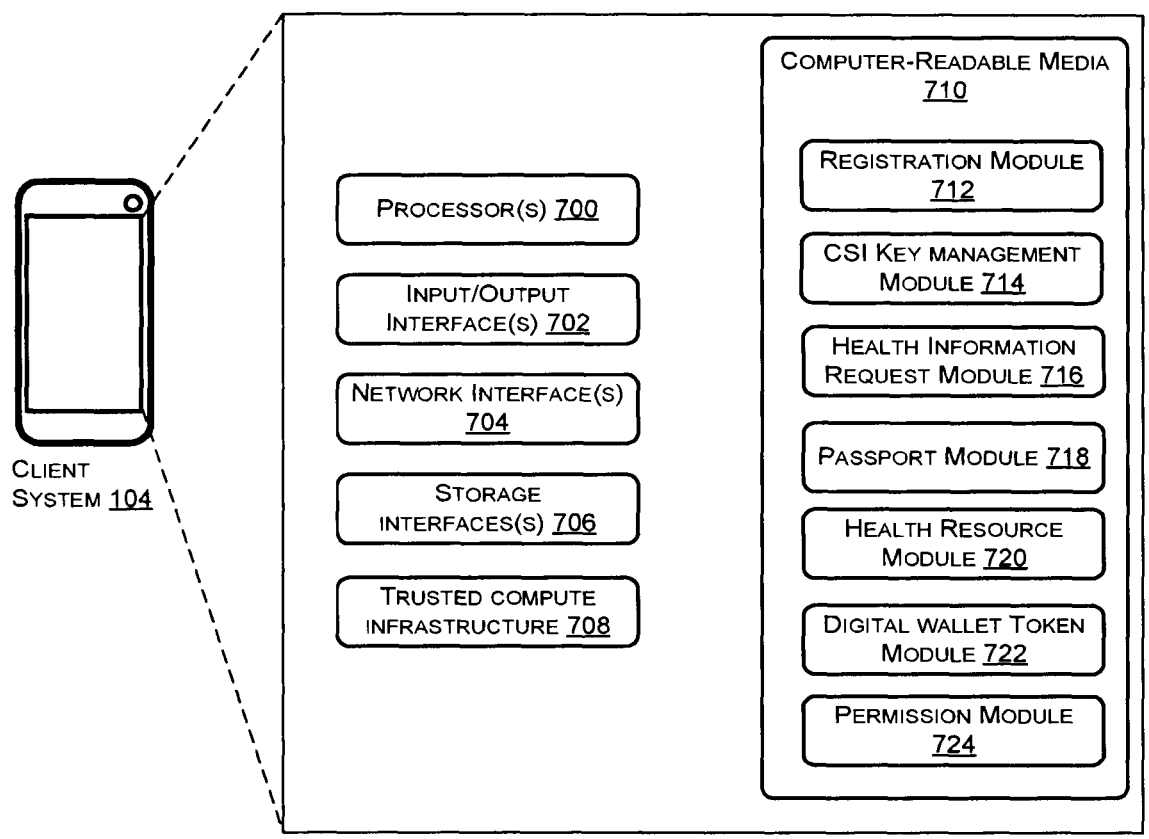
FIG. 7 is a block diagram of an example client system configured to provision, process, and/or display health information resource(s), according to example embodiments of the disclosure.

FIG. 7 is a block diagram of an example client device 104 configured to process, provision and display HIR and other information, according to example embodiments of the disclosure.

In the illustrated implementation, the client device 104 includes one or more processors 700, input/output interface(s) 702, network interface(s) 704, storage interface(s) 706, trusted compute environment 708, and computer-readable media 710. In some implementations, the processors(s) 700 may include a central processing unit (CPU), a graphics processing unit (GPU), both CPU and GPU, a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 700 may possess its own local memory, which also may store program modules, program data, and/or one or more operating systems.

The input/output interface(s) 702 may include any suitable interface for engaging with users 102, such as touch screens, a mouse, a display, or the like. The network interface(s) 704 may enable the interfacing with the one or more network(s) 110 by way of wireline and/or wireless interfaces of any suitable standard. The storage interface(s) 706 enable processor(s) 700 to access any suitable storage and/or memory device, including the computer-readable media 710, internal datastores, external datastores, cloud datastores, or the like. The trusted compute environment 708 may include cryptographic key(s) of the user.

The computer-readable media 710 may include volatile and nonvolatile memory, removable and non-removable media implemented in any method or technology for storage of information, such as computer-readable instructions, data structures, program modules, or other data. Such memory includes, but is not limited to, RAM, ROM, EEPROM, flash memory or other memory technology, CD-ROM, digital versatile discs (DVD) or other optical storage, magnetic cassettes, magnetic tape, magnetic disk storage or other magnetic storage devices, RAID storage systems, or any other medium which can be used to store the desired information and which can be accessed by a computing device. The computer-readable media 710 may be implemented as computer-readable storage media (CRSM), which may be any available physical media accessible by the processor(s) 700 to execute instructions stored on the memory 710. In one basic implementation, CRSM may include random access memory (RAM) and Flash memory. In other implementations, CRSM may include, but is not limited to, read-only memory (ROM), electrically erasable programmable read-only memory (EEPROM), or any other tangible medium which can be used to store the desired information and which can be accessed by the processor(s) 700.

Several modules such as instruction, data stores, and so forth may be stored within the computer-readable media 710 and configured to execute on the processor(s) 700. A few example functional modules are shown as applications stored in the computer-readable media 710 and executed on the processor(s) 700, although the same functionality may alternatively be implemented in hardware, firmware, or as a system on a chip (SOC). Some example modules, as stored on the computer-readable media 710, may include a registration module 712, a CSI key module 714, an HIR request module 716, a passport module 718, a health information resource module 720, a digital wallet token module 722, and a permission module 724. It will be appreciated that one or more of these modules may be installed on the client system 104 by the download of a healthcare application and/or the binding of a CSI to the healthcare application on the client system 104.

In example embodiments, the registration module 712 may include instructions executable by the processor(s) 700 to cooperate with the one or more value-added certificate authorization system(s) 160 to enable a user 102 to generate a sovereign identity. The instructions, therefore may enable the generation of a sovereign identification that may be certified, thereby establishing a CSI for the user 102.

In example embodiments, the CSI key module 714 may include instructions executable by the processor(s) 700 to manage a CSI, and any keys thereof, of a user 102. The instructions, therefore may enable the storage and use of a private key of the CSI. During the binding process of FIG. 4, the CSI, and any keys thereof, may be stored on the computer-readable media 710.

In example embodiments, the HIR request module 716 may include instructions executable by the processor(s) 700 to cooperate with the one or more blockchain system(s) 180 to enable a user 102 to acquire access token(s) pertaining to healthcare records to which the user 102 is entitled and/or permissioned. The instructions, therefore may enable the generation of a request for a particular healthcare record, which may reference a unique identifier of the that healthcare record.

In example embodiments, the passport module 718 may include instructions executable by the processor(s) 700 to maintain information associated with a user 102 and/or his or her CSI. The instructions, therefore may enable the processor(s) 700 to access personal data about an associated user 102, which may be used for the generation of a variety of requests.

In example embodiments, the health information resource module 720 may include instructions executable by the processor(s) 700 to cooperate with the one or more resource system(s) 150 to enable a user 102 to receive requested HIR. The instructions, therefore, may enable the receipt of the HIR in a standardized format, and subsequent processing, including display, thereof.

In example embodiments, the digital wallet token module 722 may include instructions executable by the processor(s) 700 to cooperate with the blockchain system(s) 180 to acquire and store access tokens associated with healthcare records. The instructions, therefore may enable the processor(s) 700 to receive the access token and store the same until a request for healthcare records is sent, to which the access token may be appended.

In example embodiments, the permission module 724 may include instructions executable by the processor(s) 700 to cooperate with the one or more value-added certificate authorization system(s) 160 to establish and/or modify permission for HIRs associated with a user 102, such as via a graphical user interface (GUI). The instructions, therefore may enable the user 102 to enter permissions, and any stipulations thereof, that he or she wishes to grant to other parties, for healthcare records that are under his or her control. The instructions may enable the processor(s) 700 to take the user's desired permissions and generate a request for establishing or changing permissions that may be sent to the value-added certificate authorization system(s) 160.

It will be appreciated that although certain functionality is described in conjunction with one or more modules 712, 714, 716, 718, 720, 722, 724, according to example embodiments, each of those functions may be enabled by instructions stored across any of those modules 712, 714, 716, 718, 720, 722, 724. Indeed, the modules 712, 714, 716, 718, 720, 722, 724 may not be discrete portions of the computer-readable media 710, but rather may be stored at any suitable location on the computer-readable media 710, such as throughout the computer-readable media 710.

Figure 8:
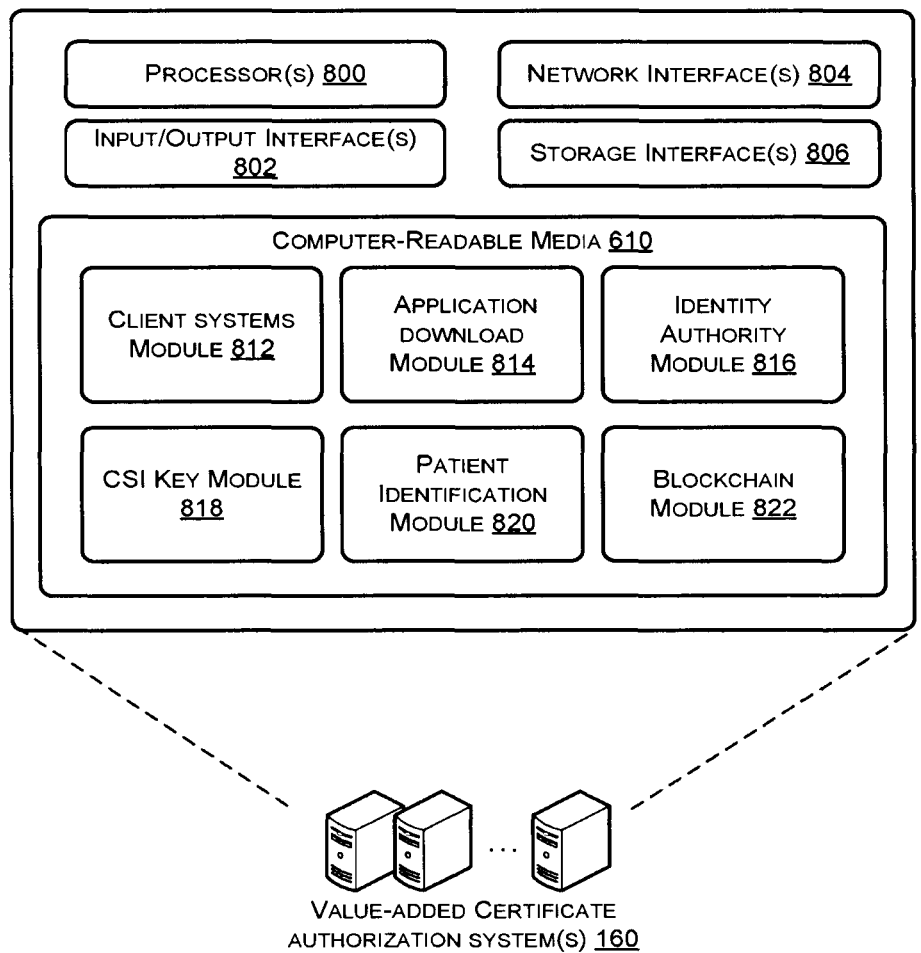
FIG. 8 is a block diagram of example value-added certificate authorization system(s) configured to issue certified self-sovereign identifier (CSI) credentials and bind CSI keys to client systems of respective users, according to example embodiments of the disclosure.

FIG. 8 is a block diagram of example value-added certificate authorization system(s) 160 configured to issue certified self-sovereign identifier (CSI) keys and bind CSI keys to client devices of respective users, according to example embodiments of the disclosure. In the illustrated implementation, value-added certificate authorization system(s) 160 include one or more processors 800, input/output interface(s) 802, network interface(s) 804, storage interface(s) 806, and computer-readable media 810. The descriptions of the one or more processors 800, the input/output interface(s) 802, the network interface(s) 804, the storage interface(s) 806, and the computer-readable media 810 may be substantially similar to the descriptions of the one or more processors 700, the input/output interface(s) 702, the network interface(s) 704, the storage interface(s) 706, and the computer-readable media 710 of FIG. 7, and in the interest of brevity, will not be repeated here.

Several modules such as instruction, data stores, and so forth may be stored within the computer-readable media 810 and configured to execute on the processor(s) 800. A few example functional modules are shown as applications stored in the computer-readable media 810 and executed on the processor(s) 800, although the same functionality may alternatively be implemented in hardware, firmware, or as a system on a chip (SOC). Some example modules, as stored on the computer-readable media 810, may include a client systems module 812, an application download module 814, an identity authority module 816, a CSI key module 818, a patient identification module 820, and a blockchain module 822.

In example embodiments, the client systems module 812 may include instructions executable by the processor(s) 800 to cooperate with one or more client system(s) 104 to enable user(s) 102 to establish their CSIs. The instructions, therefore, may enable the receipt of requests for access to the healthcare block chain, followed by the processes of requesting and/or receiving personal identity information from the client system 104 to verify the identity of a CSI requesting user 102.

In example embodiments, the application download module 814 may include instructions executable by the processor(s) 800 to cooperate with one or more application download system(s) 120 to verify a user's CSI and bind the user's CSI to a healthcare application downloaded to the user's client system 104. The instructions, therefore, may store the CSI of the user in an appropriate location, such as a passport module 718 or a CSI key management module 714 of a client system 104. The instructions may further enable the verification of the user 102 and his or her CSI prior to binding the CSI to the corresponding healthcare application on his or her client system 104.

In example embodiments, the identity authority module 816 may include instructions executable by the processor(s) 800 to cooperate with one or more identity authority system(s) 170 to either receive verification of a user's identity and/or receive information that allows the verification of a user's identity. The instructions, therefore, may allow sending received personal identity information from a client system 104 to a the one or more identity authority system(s) 170 and/or resource system(s) 150 for verification. Alternatively, the instructions, may enable requesting independent, third-party identity information from the one or more identity authority system(s) 170 and/or resource system(s) 150 pertaining to a user 102 for comparison to personal identity information received from a client device 104 associated with that user 102. for verification. In the latter case, the processor(s) 800 may also be configured, by executing the instructions in the identity authority module 816, to make a comparison of independent, third-party identity information and corresponding personal identity information received from a client device 104 to perform a user 102 verification for the purposes of signing a CSI.

In example embodiments, the CSI key module 818 may include instructions executable by the processor(s) 800 to sign a self-sovereign identity to provide a certified self-sovereign identity (CSI). The instructions, therefore, may enable the establishment of the CSI after verifying the identity of a user 102 and/or verifying that the user does not already have a CSI.

In example embodiments, the patient identification module 820 may include instructions executable by the processor(s) 800 to identify a user 102 in the form of a patient 102 who is to be issued a CSI and for whom the CSI is to be bound to his or her healthcare application on his or her client system 104. The instructions, therefore, may allow the verification of the user's identity and binding of the CSI to the healthcare application.

In example embodiments, the blockchain module 822 may include instructions executable by the processor(s) 800 to cooperate with one or more blockchain system(s) 180 to register a newly issued CSI, such as by hashing a public key corresponding to the signed CSI onto the healthcare blockchain. The instructions may also enable permissions for HIRs (e.g., EHR, PHI, etc.) to be established and/or updated on the healthcare blockchain. In some cases, the instructions may enable the processor(s) 800 to generate the permission smart contract(s) that are incorporated on the healthcare blockchain. In other cases, the instructions may allow the processor(s) 800 to cooperate with the blockchain system(s) 180 to generate the permission smart contract(s) that are incorporated in the healthcare blockchain.

It will be appreciated that although certain functionality is described in conjunction with one or more modules 812, 814, 816, 818, 820, 822, 824, according to example embodiments, each of those functions may be enabled by instructions stored across any of those modules 812, 814, 816, 818, 820, 822, 824. Indeed, the modules 812, 814, 816, 818, 820, 822, 824 may not be discrete portions of the computer-readable media 810, but rather may be stored at any suitable location on the computer-readable media 810, such as throughout the computer-readable media 810.

Figure 9:
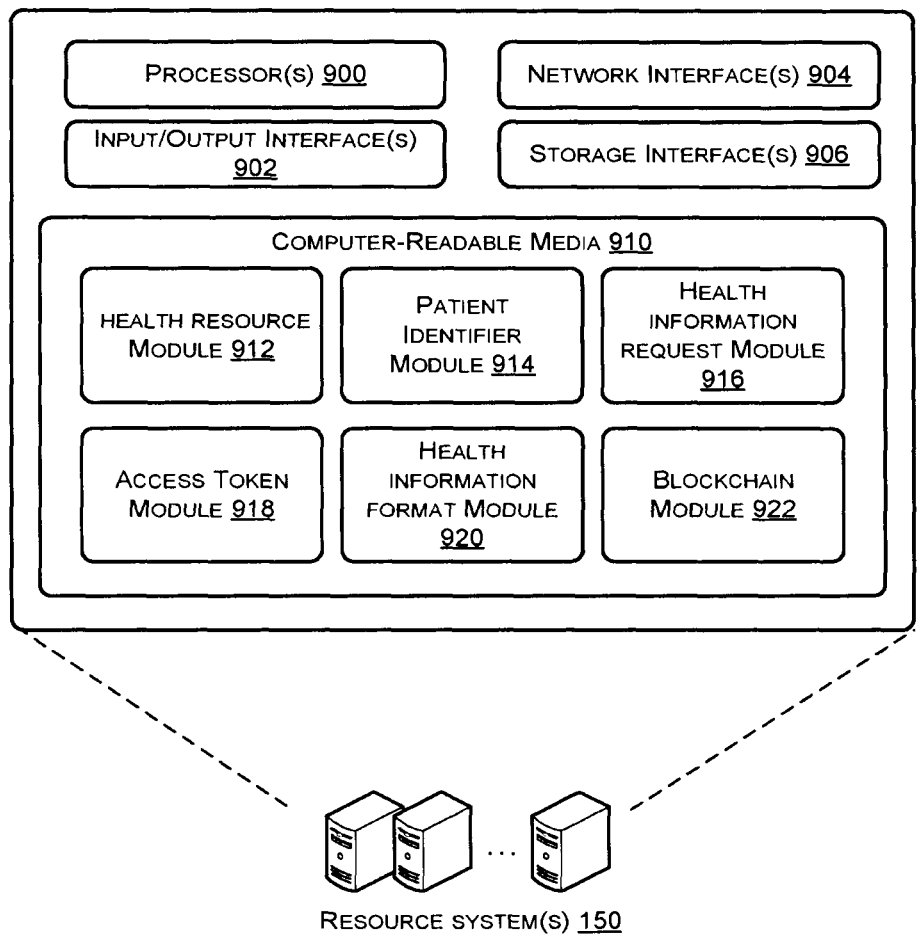
FIG. 9 is a block diagram of example resource system(s) configured to store and provide healthcare data, according to example embodiments of the disclosure.

FIG. 9 is a block diagram of example resource system(s) 150 configured to store and provide healthcare data, according to example embodiments of the disclosure. In the illustrated implementation, the resource system(s) 150 include one or more processors 900, input/output interface(s) 902, network interface(s) 904, storage interface(s) 906, and computer-readable media 910. The descriptions of the one or more processor(s) 900, the input/output interface(s) 902, the network interface(s) 904, the storage interface(s) 906, and the computer-readable media 910 may be substantially similar to the descriptions of the one or more processors 700, the input/output interface(s) 702, the network interface(s) 704, the storage interface(s) 706, and the computer-readable media 710 of FIG. 7, and in the interest of brevity, will not be repeated here.

Several modules such as instruction, data stores, and so forth may be stored within the computer-readable media 910 and configured to execute on the processor(s) 900. A few example functional modules are shown as applications stored in the computer-readable media 910 and executed on the processor(s) 900, although the same functionality may alternatively be implemented in hardware, firmware, or as a system on a chip (SOC). Some example modules, as stored on the computer-readable media 910, may include an electronic health information resource module 912, a patient identifier module 914, a HIR request module 916, an access token module 918, a health resource format module 920, and a blockchain module 922.

In example embodiments, the health information resource module 912 may include instructions executable by the processor(s) 900 to store and manage EHRs 140. In some cases, the EHRs may be received from one or more other system(s), such as client system(s) 104. These EHRs may be stored and associated with one or more user(s) 102, such as a healthcare provider 102, or a patient 102, or indeed any other stakeholder of the EHR. The instructions, therefore, may further assign an identifier, such as a unique identifier for the HER that is maintained. In some cases, the EHRs may be from a captive source, such as when the resource system(s) 150 belong to a healthcare provider who stores EHRs thereon. In other cases, the EHRs may be provided by external sources, such as a patient who may want to report his or her exercise log, or results from his/her activity tracker. Thus, the instructions, as executed by the processor(s) 900 enable intake, identification, and/or organized storage of HIRs within EHRs.

In example embodiments, the patient identifier module 914 may include instructions executable by the processor(s) 900 to identify a user 102 to whom a particular EHR may correspond. The instructions, therefore, may allow the tagging of EHRs, such as with any variety of identifiers, such as CSI and/or MRMs. In some cases, the processor(s) 900 may further be configured to receive personal identification information from the value-added certificate authorization system(s) 160 and make a determination of whether the personal identification information is valid based at least in part on personal information associated with one or more EHRs 140.

In example embodiments, the health resource request module 916 may include instructions executable by the processor(s) 900 to process a request for HIR, such as from a client system 104. The instructions, therefore, may allow the identification of the particular EHR that is being requested and determining if that EHR is available.

In example embodiments, the access token module 918 may include instructions executable by the processor(s) 900 to identify an access token (e.g., an OAuth 2 token), as received with or as part of a request for HIR. The instructions, therefore, may allow the verification and determination of validity of the access token to determine if the requested HIR is to be provided. In some cases, the instructions may enable a secondary check to identify if a notification is received from the blockchain system(s) 180 of whether requested HIR is to be disbursed.

In example embodiments, the health resource format module 920 may include instructions, such as an API, executable by the processor(s) 900 to provide a standardized, highly granular interface, with standardized labeling of data elements for providing requested HIR to client system(s) 104. The instructions, therefore, may allow the reporting, according to a set of pre-established standards for various types of HIR. For example, there may be a pre-established format for reporting blood work with granular data elements (e.g., red blood cell count, platelet count, etc.), and a different pre-established format with granular data elements for reporting strep test results.

In example embodiments, the optional blockchain module 922 may include instructions executable by the processor(s) 900 to operate as a node on the healthcare blockchain. In some cases, a resource system 150 may operate as a resource provider and EHR manager, while also operating as a node of the distributed ledger of the healthcare blockchain. The instructions in the blockchain module 922 may enable a resource system 150 to also operate as a blockchain system 180.

It will be appreciated that although certain functionality is described in conjunction with one or more modules 912, 914, 916, 918, 920, 922, 924, according to example embodiments, each of those functions may be enabled by instructions stored across any of those modules 912, 914, 916, 918, 920, 922, 924. Indeed, the modules 912, 914, 916, 918, 920, 922, 924 may not be discrete portions of the computer-readable media 910, but rather may be stored at any suitable location on the computer-readable media 910, such as throughout the computer-readable media 910.

Figure 10:
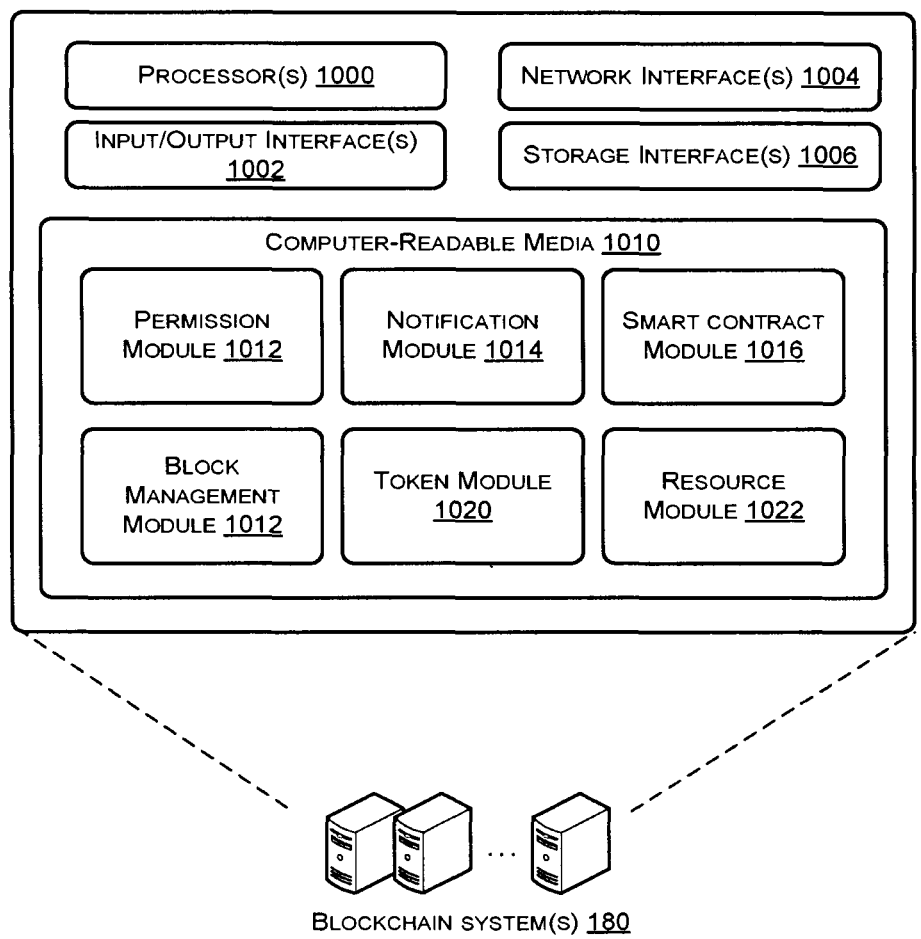
FIG. 10 is a block diagram of a node on the blockchain system(s) configured to maintain a healthcare blockchain, according to example embodiments of the disclosure.

FIG. 10 is a block diagram of blockchain system(s) 180 configured to maintain a healthcare blockchain, according to example embodiments of the disclosure. In example embodiments, multiple nodes may be interconnected in a peer-to-peer architecture to manage the healthcare blockchain.

In the illustrated implementation, the resource system(s) 180 include one or more processors 1000, input/output interface(s) 1002, network interface(s) 1004, storage interface(s) 1006, and computer-readable media 1010. The descriptions of the one or more processors 1000, the input/ output interface(s) 1002, the network interface(s) 1004, the storage interface(s) 1006, and the computer-readable media 1010 may be substantially similar to the descriptions of the one or more processors 700, the input/output interface(s) 702, the network interface(s) 704, the storage interface(s) 706, and the computer-readable media 710 of FIG. 7, and in the interest of brevity, will not be repeated here.

Several modules such as instruction, data stores, and so forth may be stored within the computer-readable media 1010 and configured to execute on the processor(s) 1000. A few example functional modules are shown as applications stored in the computer-readable media 1010 and executed on the processor(s) 1000, although the same functionality may alternatively be implemented in hardware, firmware, or as a system on a chip (SOC). Some example modules, as stored on the computer-readable media 1010, may include a permission module 1012, a notification module 1014, a smart contract module 1016, a block management module 1018, a token module 1020, and a resource module 1022.

In example embodiments, the permission module 1012 may include instructions executable by the processor(s) 1000 to receive instructions to establish and/or modify permissions associated with one or more EHRs. The instructions may further configure the processor(s) 1000 to generate smart contract(s) corresponding to the permissions, as received by the processor(s) 1000 and include those smart contract(s) as block(s) onto the healthcare blockchain.

In example embodiments, the notification module 1014 may include instructions executable by the processor(s) 1000 to make notifications of any transactions on the healthcare blockchain. Additionally, the instructions of the notification module 1014 may configure the processor(s) 1000 to receive notifications form other entities and include a record of the transaction onto the healthcare blockchain.

In example embodiments, the smart contract module 1016 may include instructions executable by the processor(s) 1000 to generate smart contracts to adjudicate permissions associated with an HIR. The smart contracts may issue access tokens for permissions users for access to HIRs. Additionally, the instructions in the smart contract module 1016 may enable the processor(s) 1000 to perform the instructions of the smart contracts, as they are incorporated onto the healthcare blockchain.

In example embodiments, the block management module 1018 may include instructions executable by the processor(s) 1000 to manage blocks of the blockchain, including the addition of blocks to the blockchain. The instructions, therefore, may configure the processor(s) 1000 to hash new blocks, such as blocks containing smart contracts, onto the healthcare blockchain. The instructions may also enable the processor(s) 1000 to determine, along with other blockchain system(s) 180 whether other candidate blockchain system(s) 180 are to be added as nodes of the distributed ledger. This may entail a variety of mechanisms, such as voting among blockchain system(s) 180.

In example embodiments, the token module 1020 may include instructions executable by the processor(s) 1000 to issue an access token, when requested by a client system 104 on behalf of a permissioned user. The instructions may also allow sending the access token to the requesting client system 104, such as via the one or more network(s) 110.

In example embodiments, the resource module 1022 may include instructions executable by the processor(s) 1000 to operate as a resource system 150 in those cases where the blockchain system 180 also functionally operates as a resource system 150.

It will be appreciated that although certain functionality is described in conjunction with one or more modules 1012, 1014, 1016, 1018, 1020, 1022, 1024, according to example embodiments, each of those functions may be enabled by instructions stored across any of those modules 1012, 1014, 1016, 1018, 1020, 1022, 1024. Indeed, the modules 1012, 1014, 1016, 1018, 1020, 1022, 1024 may not be discrete portions of the computer-readable media 1010, but rather may be stored at any suitable location on the computer-readable media 1010, such as throughout the computer-readable media 1010.

Figure 11:
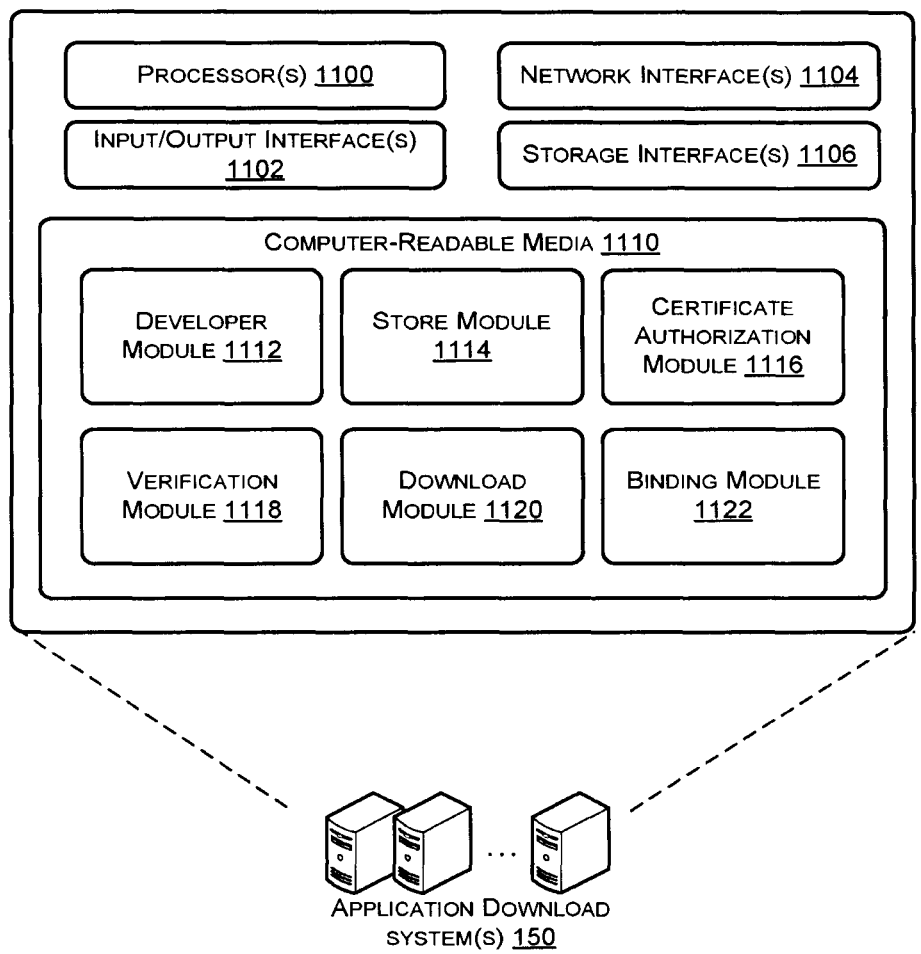
FIG. 11 is a block diagram of example application download system(s) configured to provide a healthcare application and bind the healthcare application to a user's CSI, according to example embodiments of the disclosure.

FIG. 11 is a block diagram of example application download system(s) 120 configured to provide a healthcare application and bind the healthcare application to a user's CSI, according to example embodiments of the disclosure.

In the illustrated implementation, the application download system(s) 120 include one or more processors 1100, input/output interface(s) 1102, network interface(s) 1104, storage interface(s) 1106, and computer-readable media 1110. The descriptions of the one or more processors 1100, the input/output interface(s) 1102, the network interface(s) 1104, the storage interface(s) 1106, and the computer-readable media 1110 may be substantially similar to the descriptions of the one or more processors 700, the input/output interface(s) 702, the network interface(s) 704, the storage interface(s) 706, and the computer-readable media 710 of FIG. 7, and in the interest of brevity, will not be repeated here.

Several modules such as instruction, data stores, and so forth may be stored within the computer-readable media 1110 and configured to execute on the processor(s) 1100. A few example functional modules are shown as applications stored in the computer-readable media 1110 and executed on the processor(s) 1100, although the same functionality may alternatively be implemented in hardware, firmware, or as a system on a chip (SOC). Some example modules, as stored on the computer-readable media 1110, may include a developer module 1112, a store module 1114, a certificate authorization module 1116, a verification module 1118, a download module 1120, and a binding module 1122.

In example embodiments, the developer module 1112 may include instructions executable by the processor(s) 1100 to receive healthcare applications from application developer system(s) 132, as developed by one or more application developer(s) 130. The instructions, therefore, may receive, test, and/or offer for download the healthcare application(s) as developed by various entities.

In example embodiments, the store module 1114 may include instructions executable by the processor(s) 1100 to interact with the application store system(s) 122, where healthcare application(s) may be advertised for download. The instructions, therefore, may allow the redirection of client system(s) 104 that initially access the application store system(s) 122 to acquire a healthcare application.

In example embodiments, the certificate authorization module 1116 may include instructions executable by the processor(s) 1100 to cooperate with the value-added certificate authorization system(s) 160 to bind a CSI to a healthcare application, as downloaded to a client system 104. The instructions, therefore, may pass the client system off to the value-added certificate authorization system(s) 160 for storing the user's CSI in the client system(s) digital wallet.

In example embodiments, the verification module 1118 may include instructions executable by the processor(s) 1100 to verify, prior to download of a healthcare application, that the requestor of the healthcare application has a valid CSI to access the healthcare blockchain. The instructions, therefore, may allow interacting with the healthcare blockchain, and smart contract(s) thereon, via the blockchain system(s) 180 to receive a CSI verification of a user 102.

In example embodiments, the download module 1120 may include instructions executable by the processor(s) 1100 to allow download of a healthcare application that a user 102 desires. The instructions, therefore, may allow the download of the healthcare application, such as via the one or more network(s) 110, after the CSI of a user 102 has been verified.

In example embodiments, the binding module 1122 may include instructions executable by the processor(s) 1100 to cooperate with a value-added certificate authorization system(s) 160 to bind a user's CSI to a downloaded healthcare application on a user's client system 104.

It will be appreciated that although certain functionality is described in conjunction with one or more modules 1112, 1114, 1116, 1118, 1120, 1122, 1124, according to example embodiments, each of those functions may be enabled by instructions stored across any of those modules 1112, 1114, 1116, 1118, 1120, 1122, 1124. Indeed, the modules 1112, 1114, 1116, 1118, 1120, 1122, 1124 may not be discrete portions of the computer-readable media 1110, but rather may be stored at any suitable location on the computer-readable media 1110, such as throughout the computer-readable media 1110.

Figure 12:
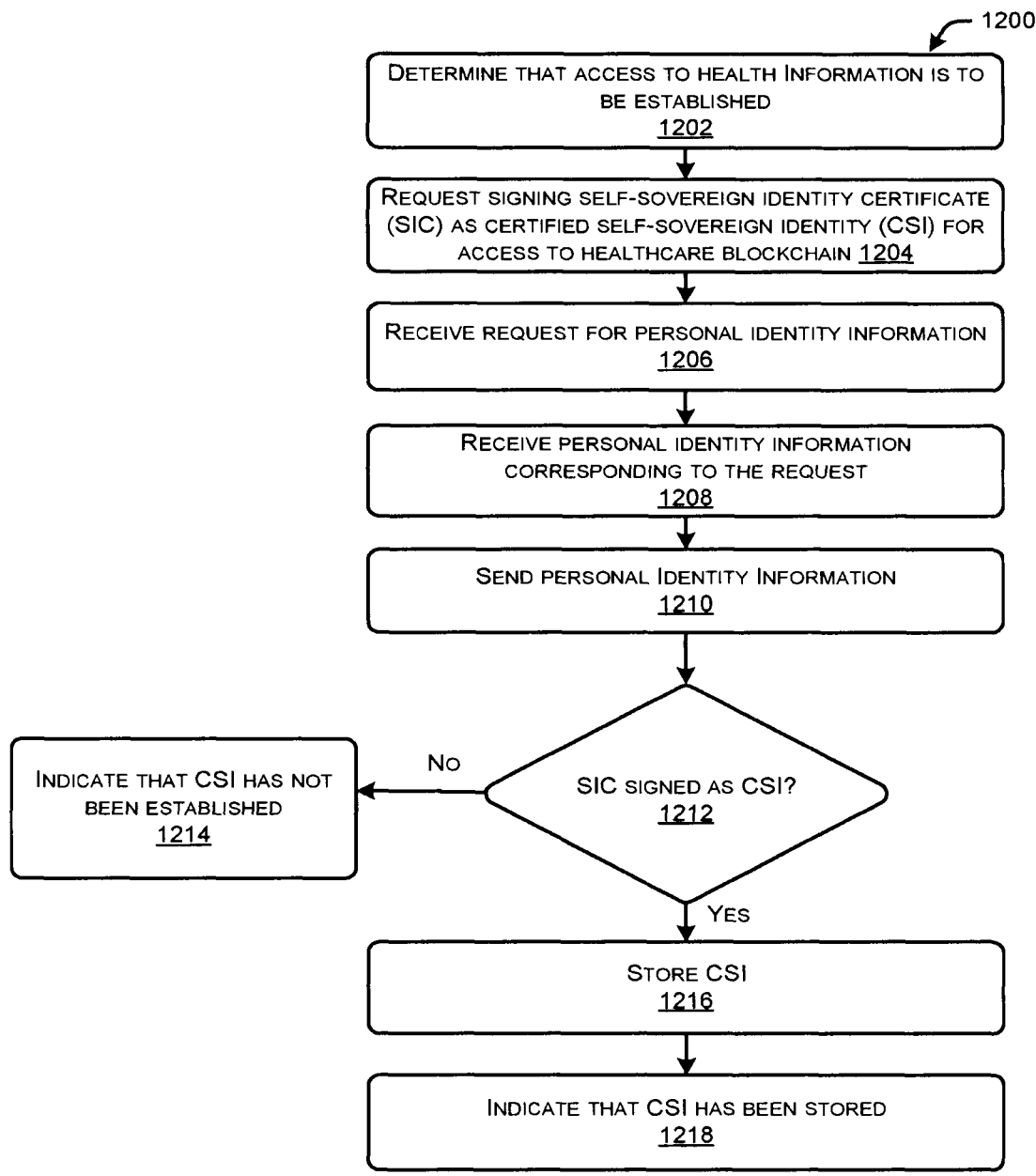
FIG. 12 is flow diagram illustrating an example method for requesting and receiving certified self-sovereign identity credentials, according to example embodiments of the disclosure.

FIG. 12 is flow diagram illustrating an example method 1200 for requesting and receiving a CSI key, according to example embodiments of the disclosure. The processes of method 1200 may be performed by a client system 104 in cooperation with one or more other entities of environment 100.

At block 1202, it may be determined that access to a health information resource (HIR) is to be established. In some cases, this access may need to be established to support a given healthcare application. This access may be for a user 102, such a user that may be interacting with the client system 104 performing the processes of method 1200. The user 102 may interact, by any suitable I/O interface of the client system 104, such as a touch screen.

At block 1204, a certified self-sovereign identity (CSI) as a signed self-sovereign identity certificate (SIC) may be requested for access to healthcare blockchain. This request may be made to the value-added certificate authorization system(s) 160 on behalf of the user 102.

At block 1206, request for personal identity information may be received. This request, in example embodiments, may be received from the value-added certificate authorization system(s) 160.

At block 1208, personal identity information corresponding to the request may be received.

At block 1210, the personal identity information may be sent. In example embodiments, the personal identity information may be sent to the value-added certificate authorization system(s) 160.

At block 1212, it may be determined if the SIC has been signed as a CSI. In example embodiments, this may entail the value-added certificate authorization system(s) 160 signing and/or registering with the blockchain the CSI associated with the user for whom access to the HIR is to be established. The CSI, in example embodiments, may be a digitally signed SIC, as described above. In example embodiments, this determination may entail the client system 104 receiving an indication that the CSI registration was successful or unsuccessful from the value-added certificate authorization system(s) 160. In other example embodiments, not receiving a confirmation from the value-added certificate authorization system(s) 160 within a predetermined period of time may be deemed by the client system(s) 104 that the CSI has not been established. In some cases, the CSI being received, as disclosed herein, may be a notification that the CSI has been signed by the value-added certificate authorization system(s) 160.

If at block 1212 the CSI is not established, then at block 1214, the CSI not being established may be indicated. This may entail displaying, to the user 102, such as on a touch screen of the client system 104, that the CSI establishment and/or the access to the healthcare blockchain was not successful.

If, on the other hand, at block 1212 the CSI was received, then at block 1016, the CSI may be stored, such as in the CSI key management module 714. In other words, at this point, the client system 104 may have a private CSI key stored thereupon for the purpose of accessing the healthcare blockchain. At this point, the value-added certificate authorization system(s) 160 may cause the corresponding public CSI key to be registered and/or hashed onto the blockchain. At block 1218, it may be indicated that the CSI has been stored.

Figure 13:
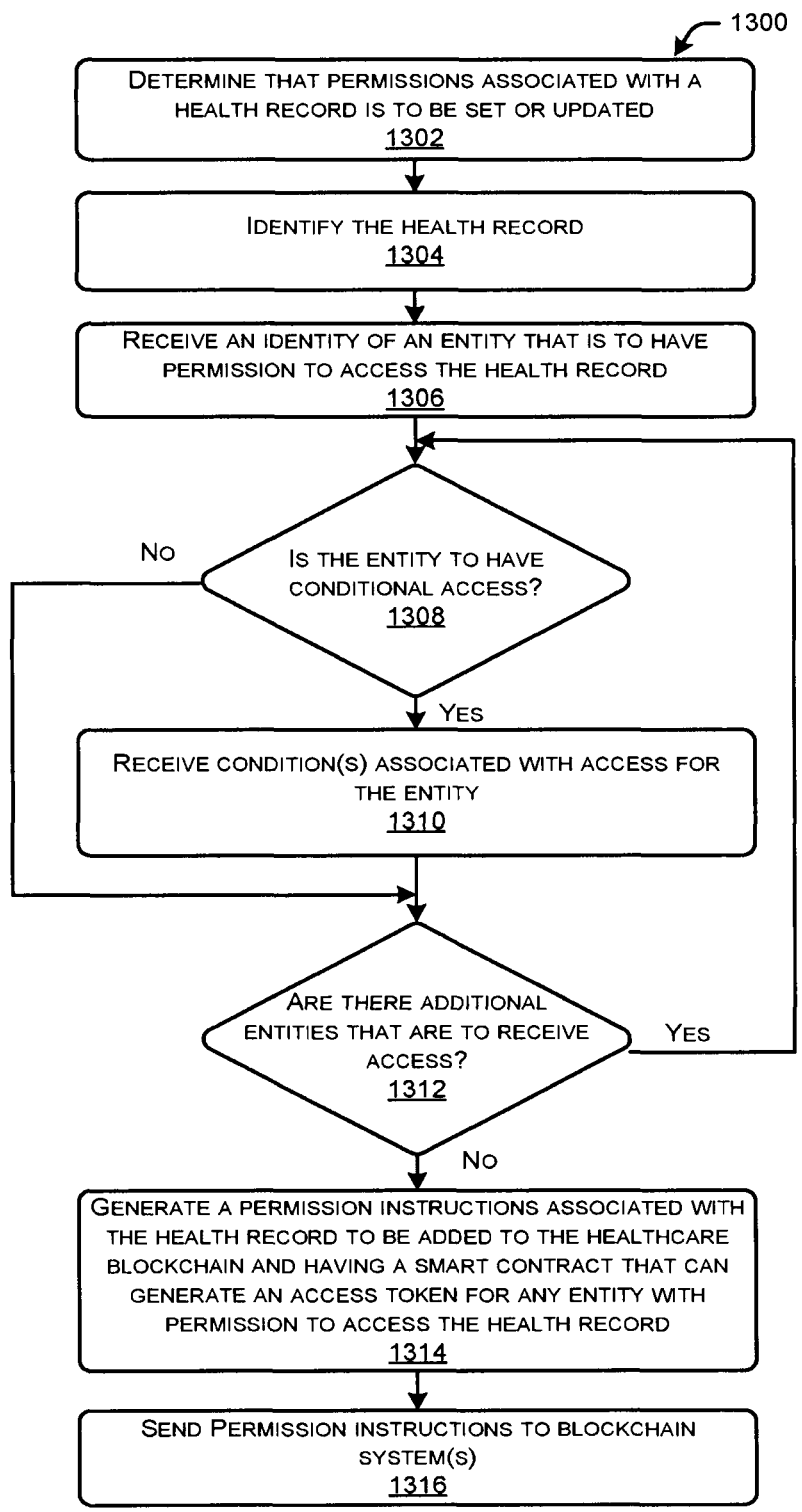
FIG. 13 is flow diagram illustrating an example method for generating and memorializing permissions within smart contracts included in a healthcare blockchain associated with healthcare records, according to example embodiments of the disclosure.

FIG. 13 is flow diagram illustrating an example method 1300 for generating and memorializing permissions associated with healthcare records, according to example embodiments of the disclosure. The processes of method 1300 may be performed by a client system 104 in cooperation with one or more other entities of environment 100.

At block 1302, it may be determined that permissions associated with an HIR are to be set or updated. This determination may be based at least in part on a user 102 indicating via one or more interactions with his or her client system 104 that he or she wishes to modify permissions for EHRs that are under his or her control.

At block 1304, the HIRs may be identified. This identification may be based at least in part in providing and/or looking up an identifier, such as a unique identifier associated with the HIR. At block 1306, an identity of an entity that is to have permission to access the HIR may be received. This indication may be entered, such as by a user 102, onto the client system 104.

At block 1308, it may be determined if the entity is to have conditional access. If it is determined that the entity is to have conditional access to the HIR, then at block 1310, the condition(s) associated with access for the entity may be received.

On the other hand, if at 1308 it is determined that the entity is not to have conditions on the access of the HIR, then the method 1300 may proceed to block 1312. Additionally, after the condition(s) for the entity are received at block 1310, the method may proceed to block 1312.

At block 1312, it may be determined if there are additional entities that are to receive access to the HIR. If there are additional entities that are to receive access to the HIR, then the method 1300 may return to block 1306 to receive an additional identity of an entity that is to receive access to the HIR.

If, however, at block 1312, it is determined that no other entities are to receive access to the HIR, then the method may advance to block 1314. At block 1314, a permission may be generated for the HIR. This permission may have a smart contract(s) that reflects the permissions and conditions thereto, as determined by the processes of blocks 1306 and 1310. The smart contract(s) may be configured to generate an access token for the HIR for any permissioned entities. At block 1316, the permission may be sent to the blockchain system(s). The blockchain system(s) 180, upon receiving the permission may be configured to include the permission in the healthcare blockchain, such as by hashing the permissions onto the healthcare blockchain.

Figure 14:
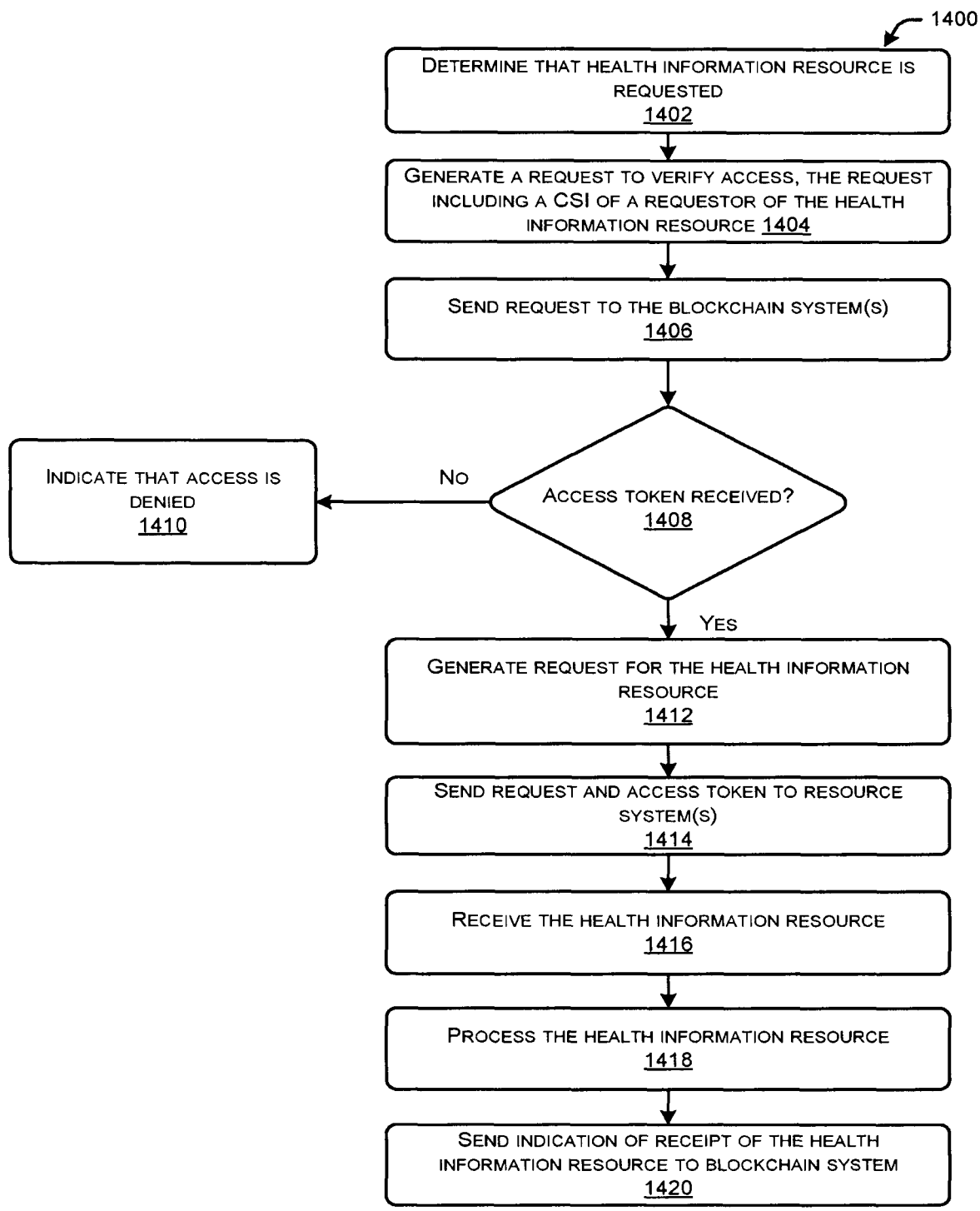
FIG. 14 is flow diagram illustrating an example method for obtaining health information resource(s) (HIRs) and creating a record of the receipt of the HIRs, according to example embodiments of the disclosure.

FIG. 14 is flow diagram illustrating an example method 1400 for obtaining HIR and creating records of the receipt of the HIR, according to example embodiments of the disclosure. The processes of method 1400 may be performed by a client system 104 in cooperation with one or more other entities of environment 100.

At block 1402, it may be determined that HIR is requested. This request may be from a user 102 interacting with the client system 104 indicating that HIR is to be obtained. At block 1404, a request to verify access may be generated, where the request includes a CSI of the requestor of the HIR. At block 1406, the request may be sent to the blockchain system(s) 180, such as via the one or more network(s) 110.

At block 1408, it may be determined if an access token is received. If it is determined that the access token is not received, then at block 1410, it may be indicated that the access to the requested HIR was denied. If, however, at block 1408, the access token is received, then at block 1412, a request for the HIR may be generated. At block 1414, the request for the HIR, along with the access token may be sent to the resource system(s) 150, such as via the one or more network(s) 110.

At block 1416, the HIR may be received from the resource system(s) 150. At block 1418, the HIR may be processed. Processing may entail analyzing, storing, displaying, or the like.

At block 1420, an indication of receipt of the HIR may be sent to the blockchain system(s). It should be appreciated that in some blockchain embodiments, the process of requesting and granting CSIs, permissions, tokens, itself propagates an immutable record of all transfers and transactions on all blockchain nodes thus rendering supplemental notifications moot.

Figure 15:
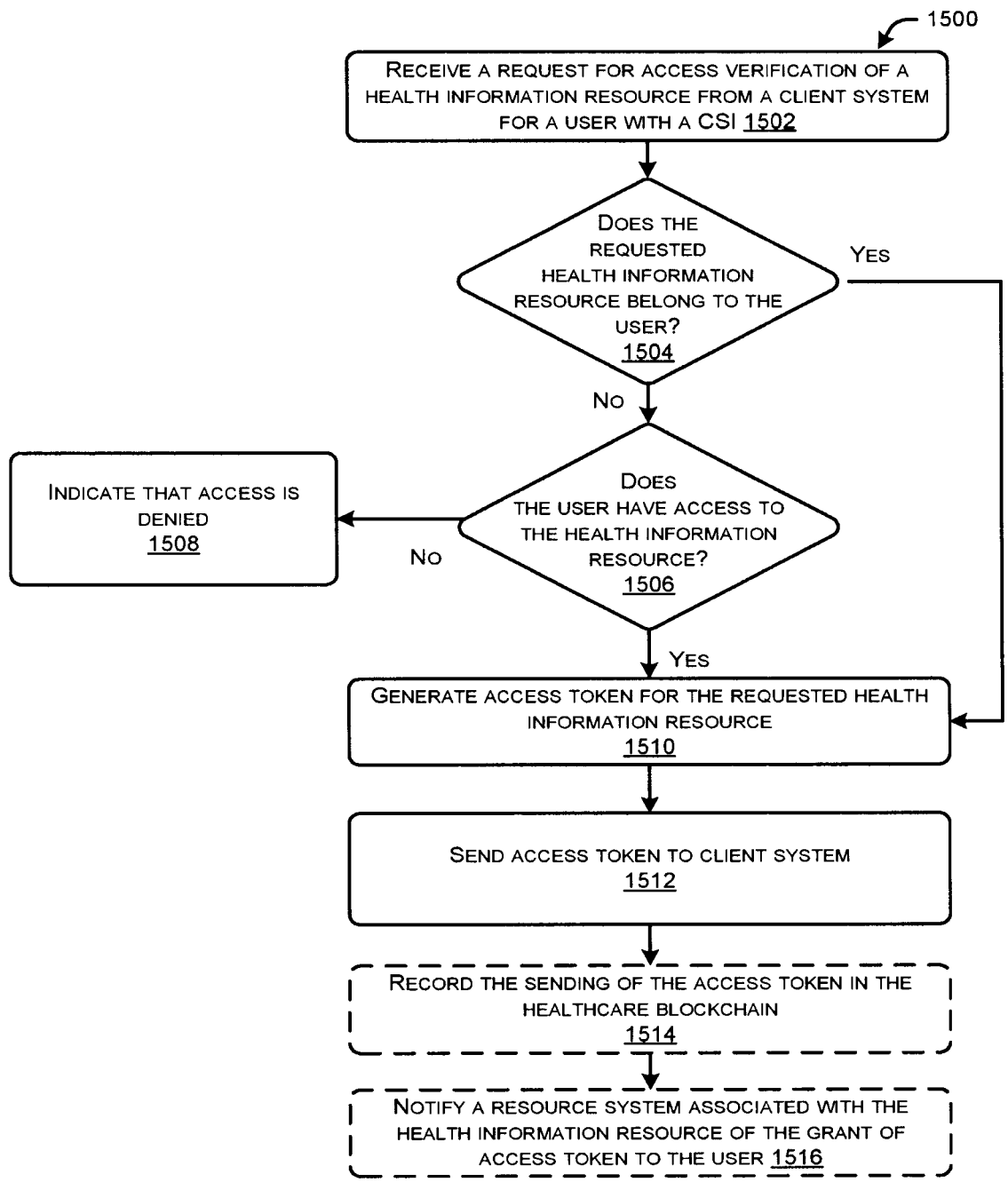
FIG. 15 is flow diagram illustrating an example method for processing a request for an access token and sending an access token to a client device, according to example embodiments of the disclosure.

FIG. 15 is flow diagram illustrating an example method 1500 for processing a request for an access token and sending an access token to a client device, according to example embodiments of the disclosure. The processes of method 1500 may be performed by a blockchain system 180 by executing smart contracts, as incorporated in the healthcare blockchain, in cooperation with one or more other entities of environment 100.

At block 1502, a request for access verification of an HIR from a client device for a user with a CSI may be received. At block 1504, it may be determined if the requested HIR belongs to the user. If the requested HIR does not belong to the user, then at block 1306, it may be determined whether the user has access to HIRs.

If it is determined, at block 1506, that the user does not have access to the HIR, then at block 1508, there may be an indication sent that access is denied. If, on the other hand, it is determined that the user does have access to the HIR, then at block 1510, an access token may be generated for the requested HIRs.

At block 1512, the access token may be sent to the client system 104. At block 1514, the transaction of the access token in the healthcare blockchain may be recorded. At block 1516, a resource system associated with the HIR of the grant of access token to the user may be notified.

Figure 16:
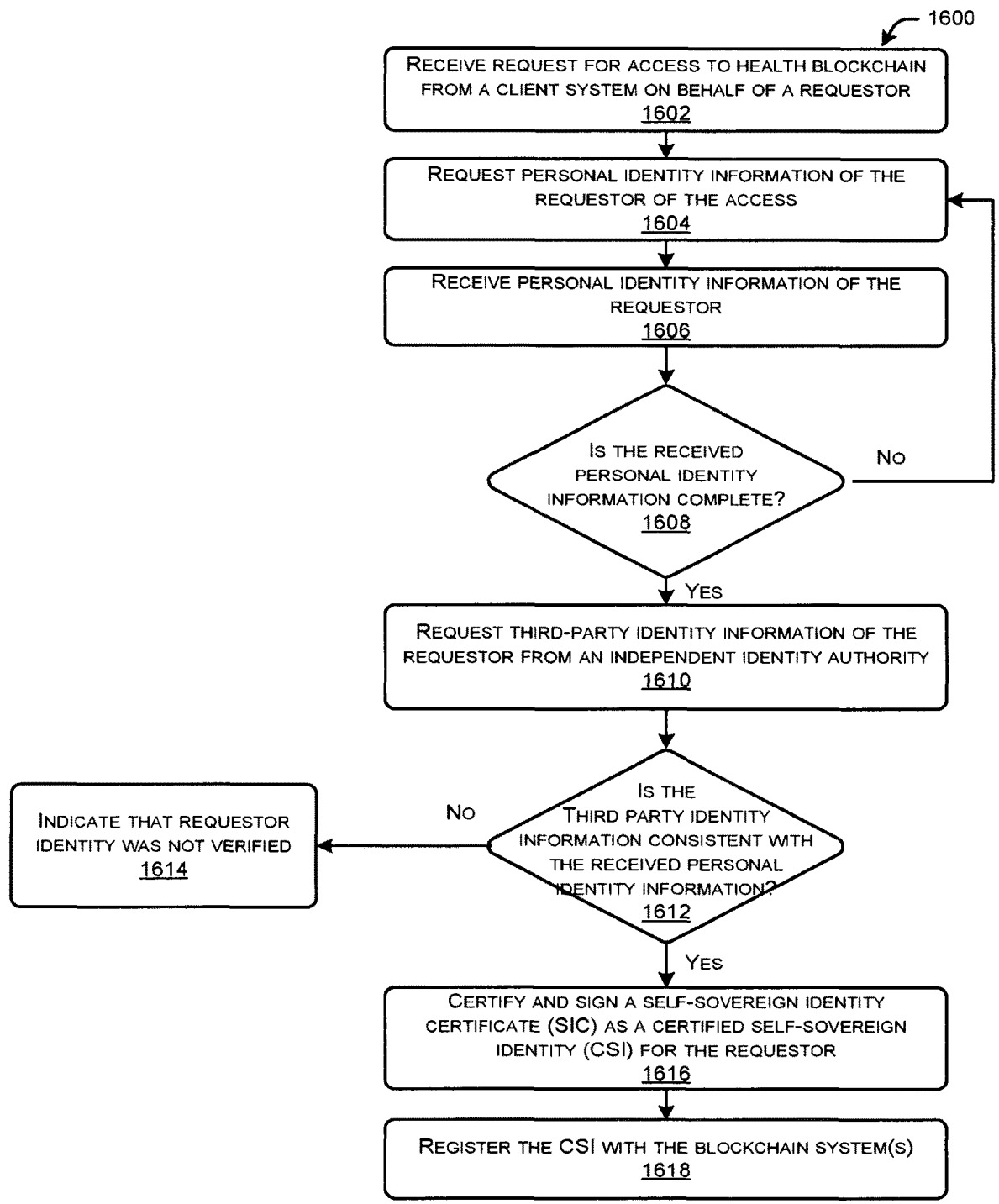
FIG. 16 is flow diagram illustrating an example method for issuing a certified self-sovereign identity (CSI) credentials and registering the CSI with the blockchain system(s), according to example embodiments of the disclosure.

FIG. 16 is flow diagram illustrating an example method 1600 for issuing a CSI key and registering the CSI key with the blockchain system(s), according to example embodiments of the disclosure. The method 1600 may be performed by the value-added certificate authorization system(s) 160 in cooperation with one or more other entities of environment 100.

At block 1602, a request for access to a healthcare blockchain from a client system for a user with a CSI may be received.

At block 1604, personal identity information for the requestor of the access may be requested.

At block 1606, personal identity information of the requestor may be received.

At block 1608, it may be determined if the received personal identity information is complete. If it is determined that the personal identity information is not complete, then the method 1600 may return to block 1604 to query personal identity information elements not provided. If, on the other hand, it is determined that the received personal identity information received is complete, then the method 1600 may proceed to block 1610.

At block 1610, a request may be sent to an independent identity authority for third party identity information about the requestor.

At block 1612, it may be determined if the third-party identity information is consistent with the received personal identity information. If the third-party identity information is not consistent with the received personal identity information, then at block 1614, there may be an indication sent that the requestor was not verified. However, if at block 1612 it is determined that the third-party identity information is indeed consistent with the received personal identity information, then the method 1600 may proceed to block 1616.

At block 1616, a self-sovereign identity may be signed to establish a certified self-sovereign identity (CSI).

At block 1618, the CSI may be registered with the blockchain system(s) 180. This may entail hashing a block containing a private key of the CSI onto the healthcare blockchain.

Figure 17:
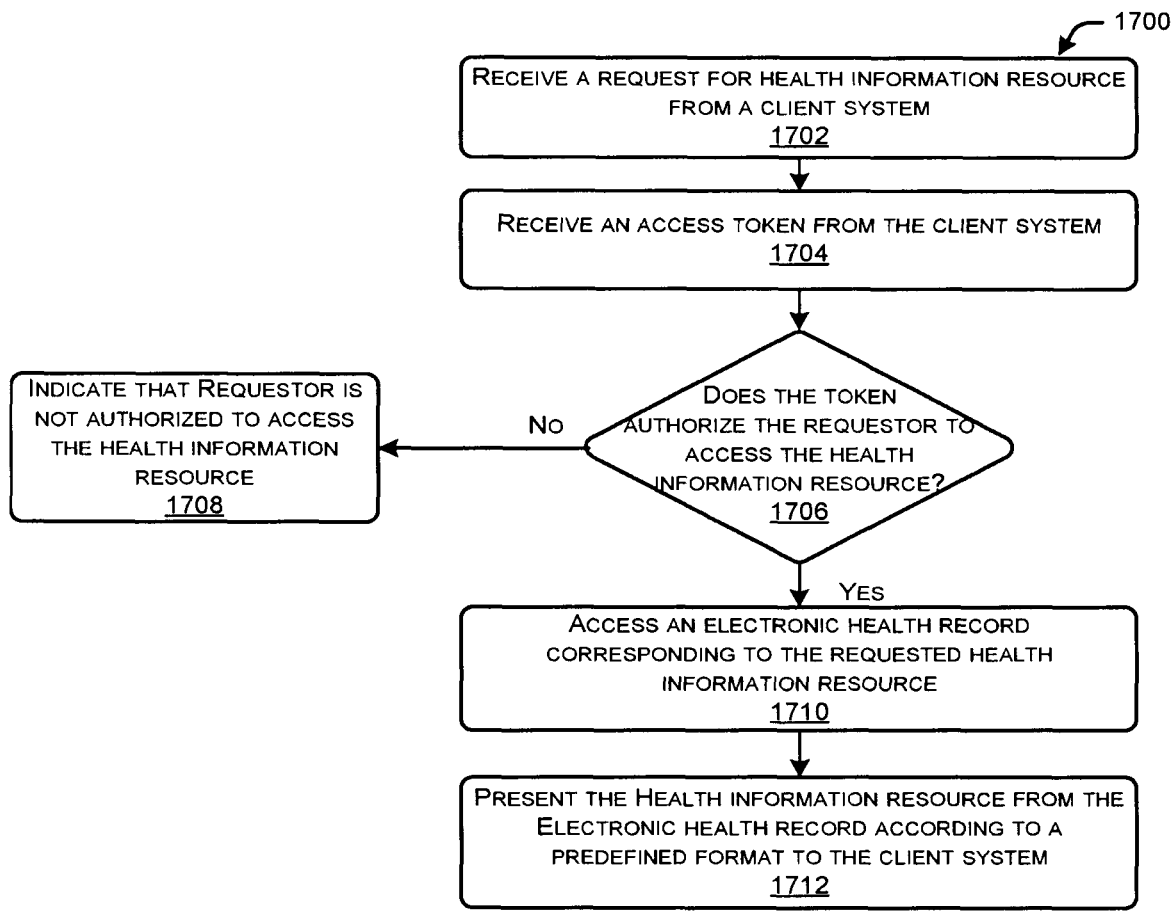
FIG. 17 is flow diagram illustrating an example method for providing health information resource(s) to a client device, according to example embodiments of the disclosure.

FIG. 17 is flow diagram illustrating an example method 1700 for providing HIRs to a client device, according to example embodiments of the disclosure. The method 1700 may be performed by one or more resource system(s) 150 in cooperation with one or more entities of environment 100. At block 1702, a request for an HIR may be received from a client system 104. At block 1704, an access token may be received from the client system 104.

At block 1706, it may be determined if the access token authorizes the requestor to access the requested HIR. If the access token does not allow the access of the requested HIR, then at block 1708, it may be indicated that the requestor is not authorized to access the requested HIR. However, if at block 1506 it is determined that the access token does authorize the requestor to access the requested HIR, then the method 1700 may proceed to block 1710.

At block 1710, an EHR corresponding to the requested HIR may be accessed. At block 1712, the HIR from the EHR may be presented according to a predefined format to the client system 104.

Figure 18:
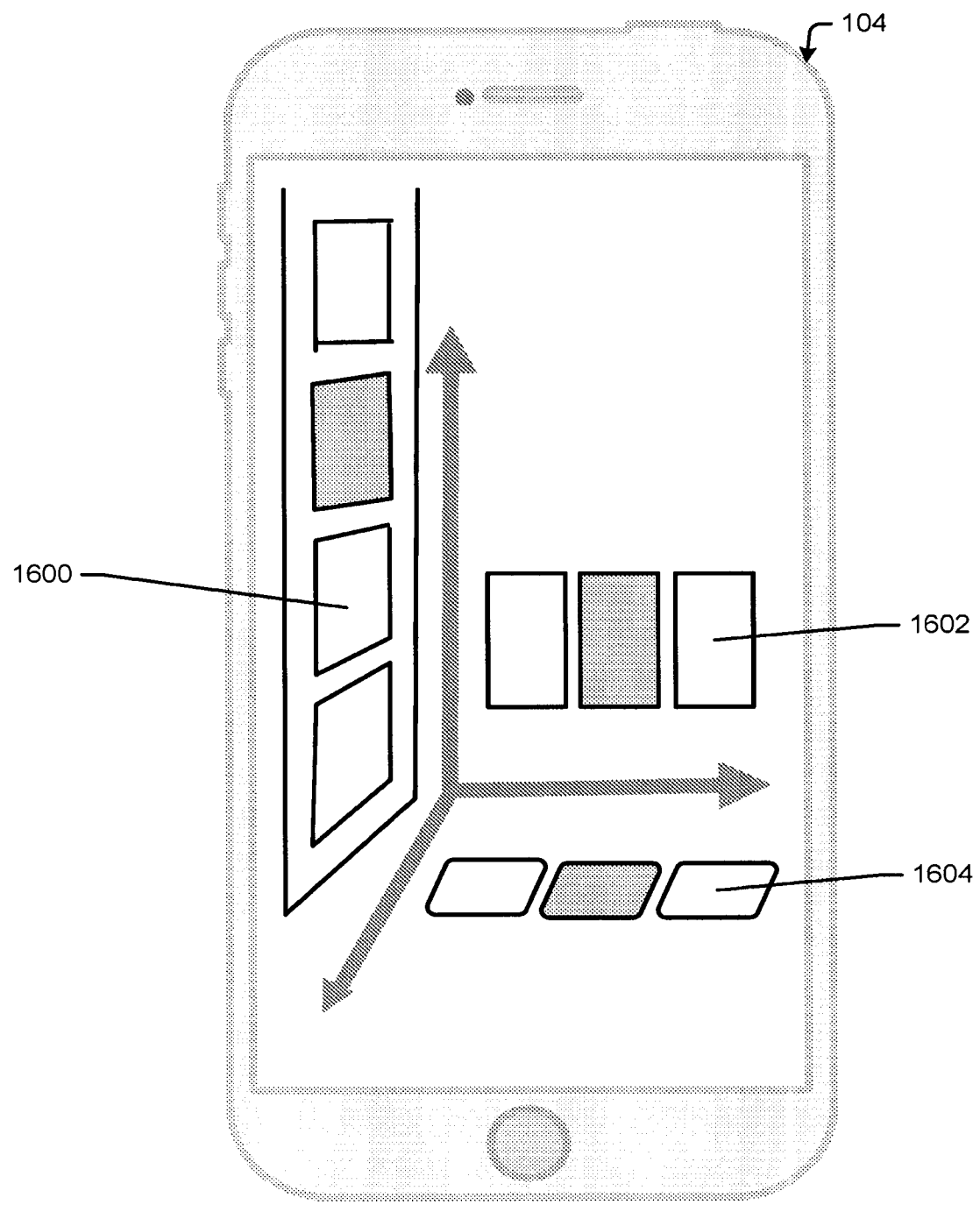
FIG. 18 is schematic diagram illustrating an example user interface on a client system for enabling user to manage permissions and/or conditions thereof, according to example embodiments of the disclosure.

FIG. 18 is schematic diagram illustrating an example user interface on a client device for enabling a user 102 to review, revoke or modify permissions and conditions thereof, according to example embodiments of the disclosure. The permissions, in example embodiments, may be presented in an orthogonal three-dimensional manner, as shown. It will be appreciated that according to example embodiments, there may be a variety of mechanisms for displaying and/or setting permissions of HIR. On the vertical axis may be a gallery 1600, there may be a number of healthcare applications to which the user 102 has, or could have, subscribed.

On the horizontal axis 1602, there may be a number of other users that may have been granted permissions to a variety of HIRs associated with the applications arrayed in the vertical axis gallery 1600. And on the applicate (or forward-extending depth) axis 1604 there may be a variety of conditions to which the additional users 102 access to HIRs may be restricted.

Figure 19:
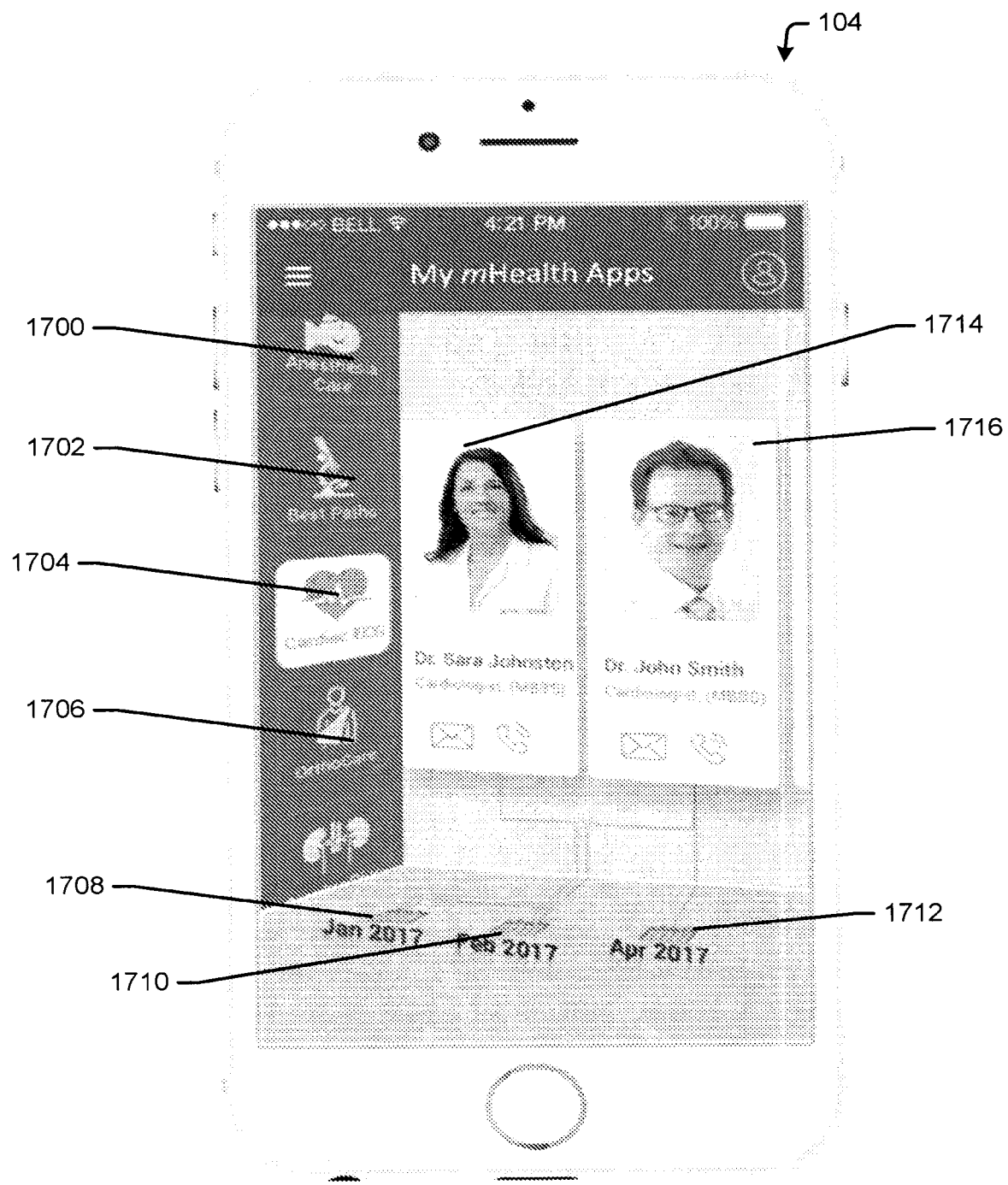
FIG. 19 is schematic diagram illustrating an example three-dimensional user interface on a client system for enabling user to review, revoke or modify permissions and conditions thereof, according to example embodiments of the disclosure.

FIG. 19 is illustrative screen shot example of a three-dimensional user interface on a client device for enabling user to review, revoke or modify permissions and conditions thereof, according to example embodiments of the disclosure. As shown, there may be a first user 1714, and a second user 1716 who may be accorded permissions to access HIRs that attend the applications to which the first user has subscribed 1700, 1702, 1704, 1706 subject to the conditions and restrictions set by the first user 102 and/or authorized other users 102. This interface, in example embodiments, may be interactive to allow a user 102 of client device 104 to set permissions for user(s) 1714, 1716. The mechanism by which the user 102 scrolls along the various axis, expands or contract viewing area(s), activate various fields, or the like, may vary with the operating systems of the user's client system 104. Further, individual application developers 130 may exert wide discretion in other user interface and/or experience (UiX) design and functional innovations, all of which are not to be limited by the illustrative Figures and descriptions as discussed herein, and are indeed included in the embodiments disclosed herein.

Figure 20:
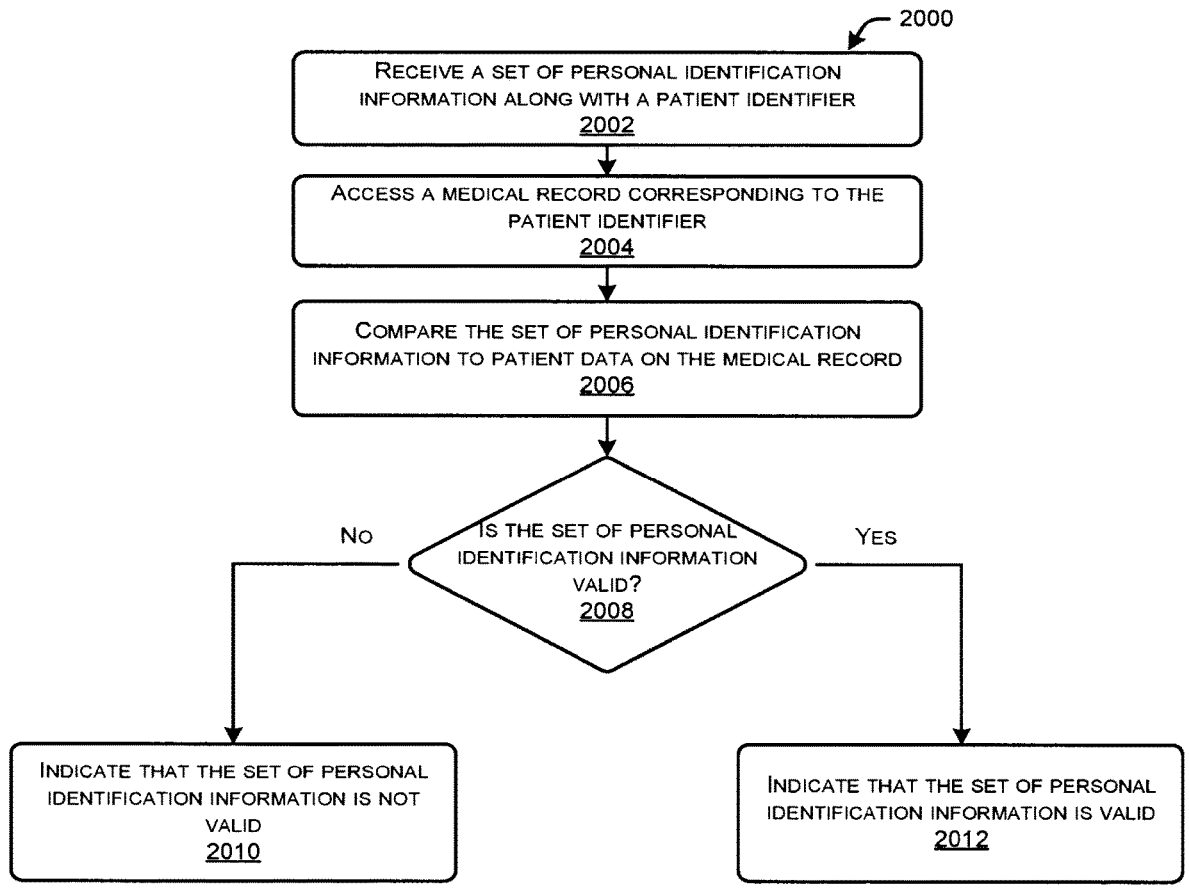
FIG. 20 is flow diagram illustrating an example method for verifying personal identification information by requesting verification from a new resource server, according to example embodiments of the disclosure.

FIG. 20 is flow diagram illustrating an example method for verifying personal identification information, according to example embodiments of the disclosure. The method 2000 may be performed by the resource system(s) 150 in cooperation with one or more other entities of environment 100 for verifying personal identification information using a preexisting medical record or EHR 140.

At block 2002, a set of personal identification information may be received along with a patient identifier. In some cases, other suitable identifier(s) of the user 102 may be provided, other than a patient identifier. When a patient identifier is provided, the patient identifier may, in some cases, be a unique patient identifier (UPI), an identifier that is associated with a healthcare provider or other entity associated with the resource system(s) 150 receiving the personal identification information, or any other suitable patient identifier. The set of personal identification information may be received from the value-added certificate authorization system(s) 160 as part of a request to make a determination of whether the personal identification information is valid based at least in part on personal information associated with one or more EHRs 140 or other personal data available to the resource system(s) 150.

At block 2004, a medical record corresponding to the patient identifier may be accessed. In some cases, this medical record may be an EHR 140 associated with the user 102 associated with the set of personal identification information. This medical record may exist, under the management of the resource system(s) 150, prior to the procedure to verify the set of personal identification information, as disclosed herein.

At block 2006, the set of personal identification information may be compared to patient data on the medical record. The patient data on the medical record may include data elements that may correspond to data elements of the set of personal identification information, such as name, date of birth, last medical check-up, etc. An element by element comparison may be performed for one or more elements of the set of personal identification information may be performed.

At block 2008, it may be determined if the set of personal identification information is valid. There may be any variety of criteria to determine if the set of personal identification information validates the user 102 to whom the set of personal identification information pertains. For example, the comparison of the process of block 2006 may be used to determine if a threshold number and/or percentage of data elements of the set of personal identification information is verified to be true based at least in part on the medical record corresponding to the user 102. Alternatively or additionally, there may be particular data elements of the set of personal identification information that must match previous record(s), such as the medical record, for the user 102 associated with the set of personal identification information to be validated. In some cases, the resource system(s) 150 may use a variety of medical records to make a determination of validity of the user.

If at block 2008 it is determined that the set of personal information is not valid, then an indication of that invalidity may be indicated at block 2010. In some cases, the resource system(s) 150 may indicate to the value-added certificate authorization system(s) 160 that the user is not validated. If, on the other hand, at block 2008 it is determined that the set of personal information is valid, then an indication of that validity may be indicated at block 2012. In some cases, the resource system(s) 150 may indicate to the value-added certificate authorization system(s) 160 that the user is validated, or otherwise who he or she claims to be.

Figure 21:
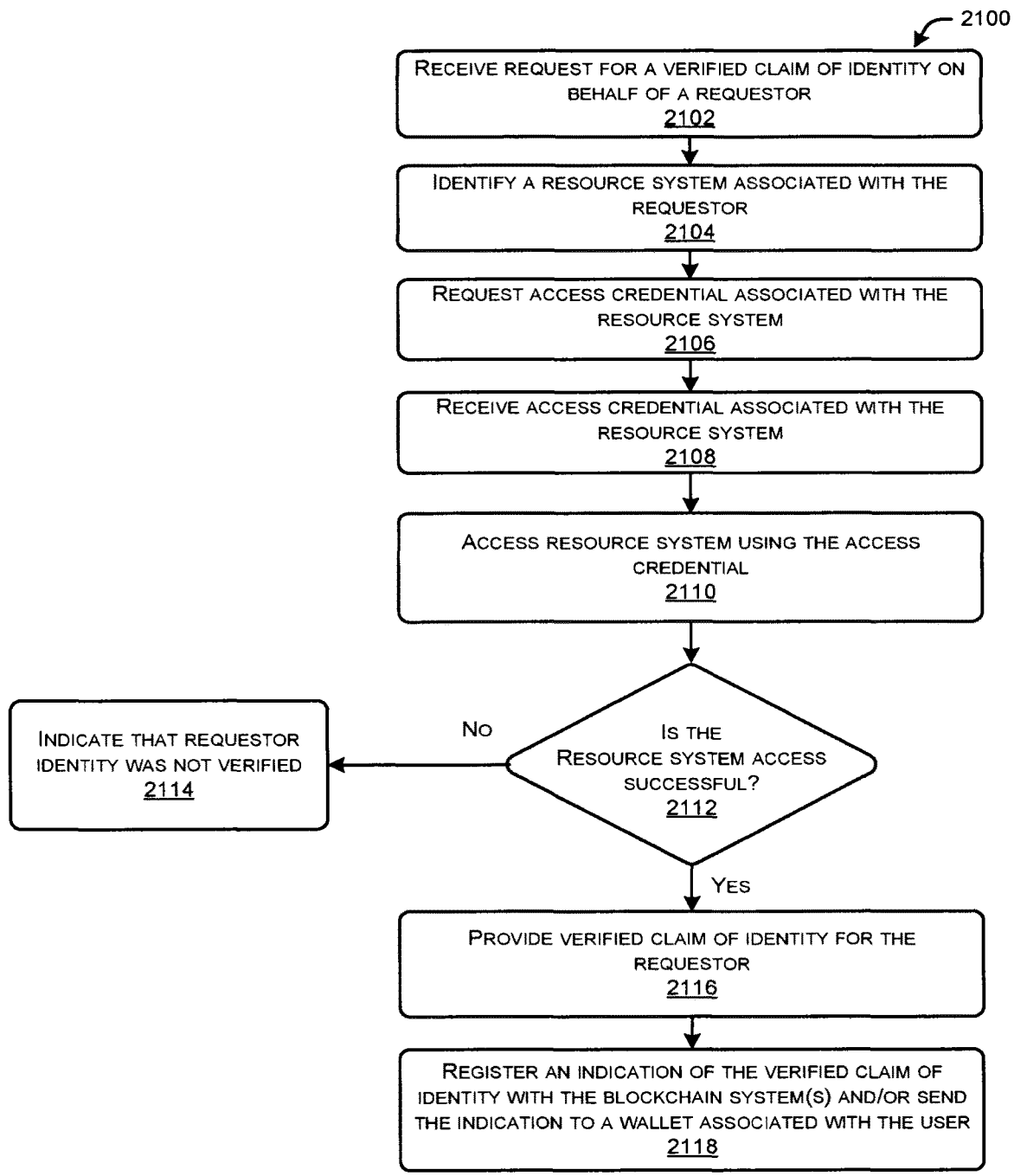
FIG. 21 is flow diagram illustrating an example method for verifying a claim of identity using access credentials of the user whose identity is to be verified, according to example embodiments of the disclosure.

FIG. 21 is flow diagram illustrating an example method 2100 for verifying a claim of identity using access credentials of the user whose identity is to be verified, according to example embodiments of the disclosure. The method 2100 may be performed by the value-added certificate authorization system(s) 160 in cooperation with one or more other entities of environment 100. The method 2100 may involve interactions with the trusted compute infrastructure 708 of a client system 104.

At block 2102, a request for a verified claim of identity may be received on behalf of a requestor. The verified claim of identity, as requested, and if verified, may allow the associated user 102 to access the healthcare blockchain, such as to access and/or set permissions for his or her health records. The request, therefore, may be to certify a self-sovereign identity that one may use via his or her client system 104 to access the healthcare blockchain and/or to access or set access to resources at a resource system 150. In example embodiments, the request may be generated locally on the client system 104 by execution one or more instructions of a software or application operating thereon. In example embodiments, the request to verify the claim of identity may be signed by the trusted compute environment 708 of the client system 104. Regardless of the mechanism of generating the request, the request may include information such as information about the user (e.g., name, DOB, etc.) of the user for whom the assertion of self-identity is being made.

At block 2104, a resource system associated with the requestor may be identified. Identifying an associated resource system 150 may entail soliciting information from the user 102 via his or her client system 104 that indicates the resource system 150 or resource system(s) 150 on which the user's EHR(s) 140 may be stored. In some cases, the user associated resource system 150 may be identified by the user providing an identity of a health care provider with which he or she has had a past relationship. In other words, the resource system 150 associated with the user 102 may be identified as the resource system 150 of a medical provider who the user 102 had used in the past for medical services. Thus, this resource system 150 may already have an electronic access account associated with the user 104. Additionally, this healthcare provider associated with the resource server 150 may have already verified the user's identity in a relatively vetted manner. For example, before healthcare services were provided to the user 102, physical indicators of the user's identity may have been checked by the healthcare provider associated with the resource system 150. For example, the user's health insurance card and driver's license may have been checked, along with identifying and/or verifying the user's medical history, allergies, emergency contact information, or the like. Thus, the resource server 150 may have a reliable verification of the user's identity due to interactions between the user 102 and the associated healthcare provider.

At block 2106, access credential associated with the resource system may be requested. In some cases, the access credential may be a login and/or password that the user 102 may use to access his or her health records at the resource system identified by the operations of block 2104. In some cases, there may be additional authentication credentials beyond a login and/or password, such as any variety of information associated with two-factor authentication or other security questions. In some cases, the access credentials may not be stored locally, or may be stored as a one-way hash of the access credentials for security reasons. In example embodiments, the requested access credential may be a service credential according to OAuth, OAuth, 2.0, or similar standards.

At block 2108, the access credential associated with the resource system may be received. This receipt of the access credential may be responsive to the request for the same provided by the operations of block 2106. The received access credential may be provided directly by the user 102, such as by the user 102 entering the access credentials on a user interface presented on his or her client device 104 responsive to the request of block 2106. In example embodiments, the received access credential may be a service credential according to OAuth, OAuth, 2.0, or similar standards.

At block 2110, the resource system may be accessed using the access credentials. In some cases, the EHRs and/or PHIs, as stored on the resource server 150, of the user may be accessed via an authentication mechanism that is a separate system from the resource server 150. Thus, that system may be accessed using the obtained access credential to verify the user. In example embodiments, the access may be granted according to OAuth, OAuth, 2.0, or similar standards.

Figure 22A:
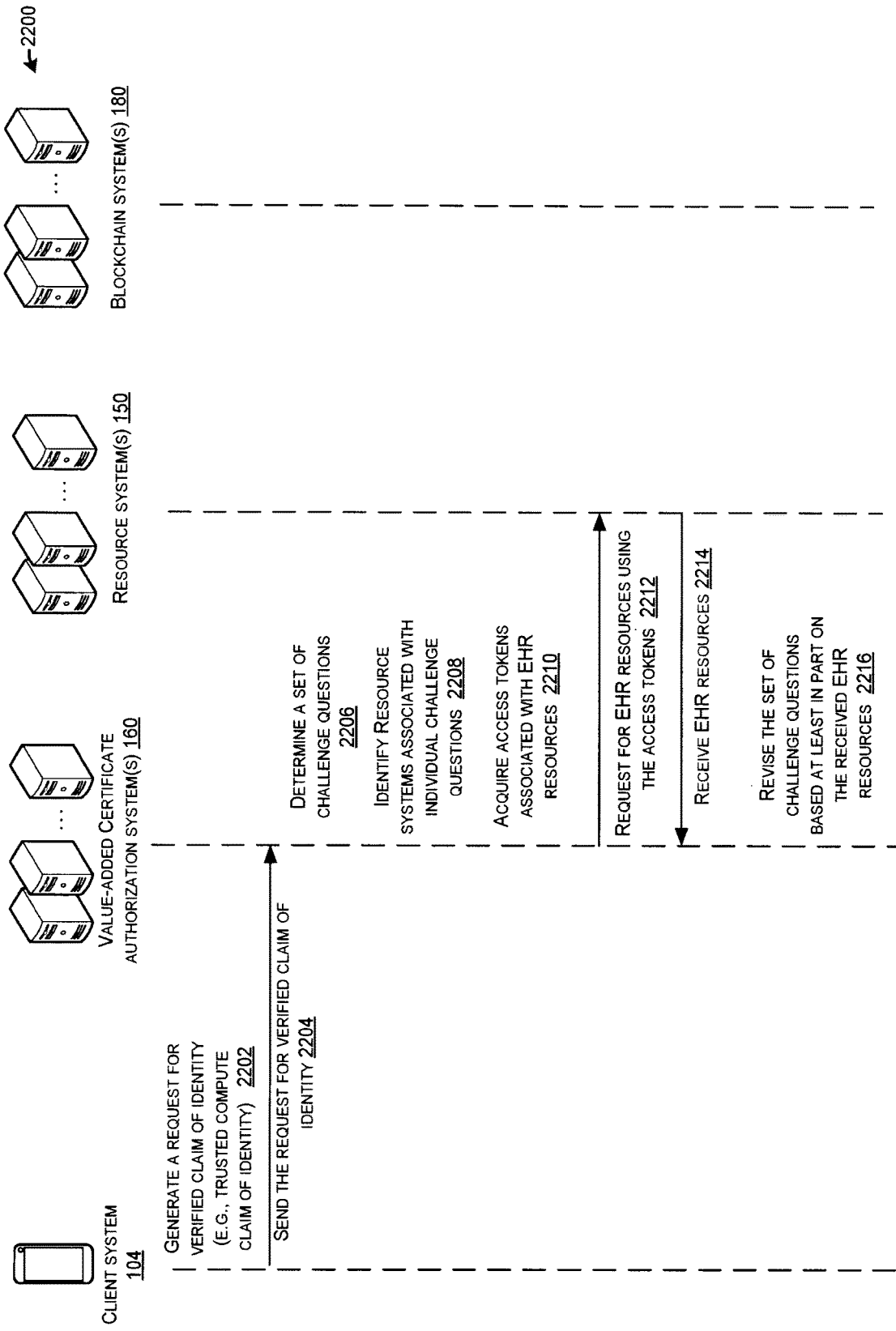
FIGS. 22A and 22B is a chart illustrating example operations for registering a client system with a certified self-sovereign identity access a healthcare blockchain by verifying user information available from a resource server, according to example embodiments of the disclosure.
Figure 22B:
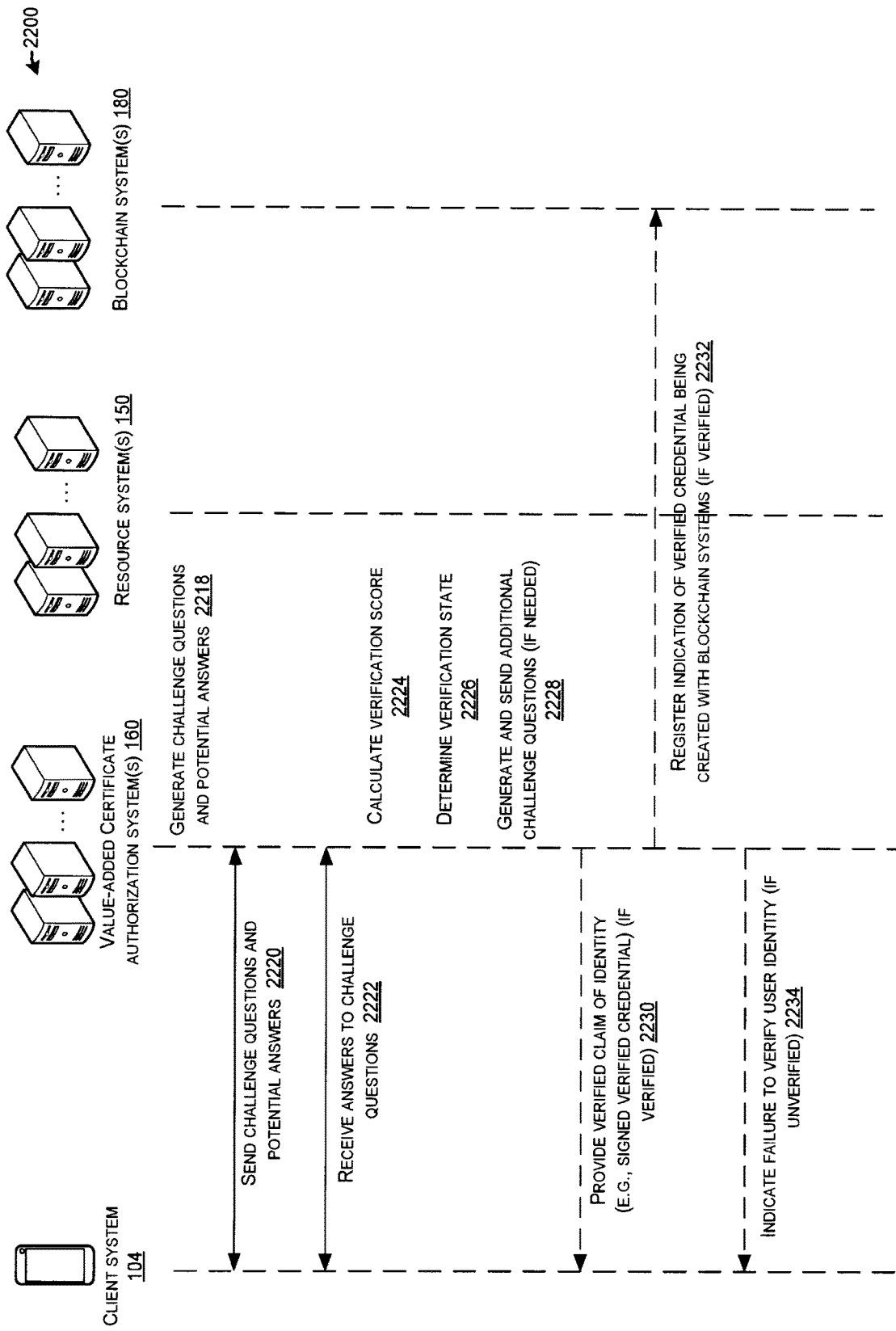

At block 2112, it may be determined if the access to the resource system was successful. This determination may entail determining that the user's health records (e.g., EHRs) are accessible on the resource system 150. If the access to the resource system was unsuccessful, then the method 2100 may proceed to 2114, where there may be an indication that the requestor's identity was not verified. In some cases, the user 102 may be able to retry the identity verification process. In other cases, other mechanisms may be used to verify the requestor's identity. For example, the method 2200 as shown in FIGS. 22A and 22B may be used to verify the user's identity if the method 2100 failed to provide a verification of the requestor. At block 2114, if it is determined that the access to the resource system was successful, then the method 2100 may proceed to block 2118.

At block 2116, a verified claim of identity may be provided for the requestor. In some cases, the verified claim of priority may be sent to the requestor's client system 104. This verified claim of identity may be stored on the client system 104 to allow the requestor to interact with the healthcare blockchain system(s) 180 to access EHRs and/or set permissions for others to access the requestor's EHRs. The verified claim of identity may include an identifier of the corresponding user 102 (e.g., requestor) and/or any other data associated with the user 102. CSI may be registered with the blockchain system(s) 180. The verified claim of identity will include a reference to a certified self-sovereign identity (CSI).

At block 2118, an indication of the verified claim of identity may be registered with the blockchain system(s) and/or issued to a wallet of the user. In other words, the resource server 150 may sign the claim of identity. This may result in an encrypted key being issued to the client system. In some cases, the key may be encrypted using the public key that corresponds to the client system's private key. This may allow the requestor to interact with the blockchain system(s) 180, such as to set permissions for his or her EHRs. In example embodiments, the blockchain system(s) 180 may receive a public key associated with the user 102 for the purpose of communicating with the user 102.

FIGS. 22A and 22B is a chart illustrating example operations 2200 for registering a client system 104 with a certified self-sovereign identity access a healthcare blockchain by verifying user information available from one or more resource systems 150, according to example embodiments of the disclosure. In this mechanism, the VACA system may reside within the enclave of medical provider along with the resource system 150. In other words, the VACA system may acquire PHI as part of method 2100, but those PHI resources may always be under the control, and within the domain of the medical provider holding the resource system 150.

The operations 2200 may include, at 2202, the client system may generate a request for a verified credential of identity. Such a verification may allow the user 102 associated with the client system 104 to access the healthcare, as maintained by the blockchain system(s) 180. In some example embodiments, the request may be generated by interacting with a web interface of a value-added certificate authorization system(s) 160 and/or by any other mechanism for interacting with value-added certificate authorization system(s) 160. In other example embodiments, the request may be generated locally on the client system 104 by execution one or more instructions of a software or application operating thereon. The request may include an assertion of identity of the user 102. In some cases, the request may be signed and/or encrypted by the trusted compute environment 708 of the client system 104.

At 2204, the request may be sent to the value-added certificate authorization system(s) 160, such as via the networks 110. In example embodiments, where the request is generated by interfacing with a web interface of the value-added certificate authorization system(s) 160, the processes 2202 and 2204 may be executed substantially concurrently and in an integrated fashion. In some cases, a user 102 as interacting with his or her client system 104 may be redirected to the value-added certificate authorization system(s) 160 to establish a verified claim of identity that may allow access to health records on the resource systems 150 and/or to the healthcare blockchain systems(s) 180 to set permissions to one's EHRs.

At 2206, a set of challenge questions may be determined. This set of challenge questions may be a preliminary set of questions about the user 102 who wishes to gain access to online health records, if answered with a sufficient level of accuracy, indicates a relatively high likelihood of identity verification.

At 2208, resource systems that may contain the information associated with the challenge questions may be identified. For example, these resource systems 150 may be associated with healthcare facilities where the user 102 has interacted with and/or received health services before.

At block 2210, access tokens may be acquired to obtain EHR resources associated with the challenge questions. These access tokens may be related to specific elements of information and for specific resource servers 150.

At 2212, EHR resources may be requested from each of the resource servers 150 where the EHR resources reside. The requests may include the corresponding access tokens for the individual EHR resources. At 2214, some or all of the EHR resources may be received from their corresponding resource servers 150.

Upon receiving the EHR resources including personal information about the user whose identity is to be verified, at block 2216, the set of challenge questions may be revised based at least in part on what EHR resources were successfully obtained. Thus, questions may be formulated based at least in part on the EHR resources that are available for such purposes, and the personal information indicated therein.

At 2218, challenge questions and potential answers may be generated. For example, a question may ask about specific information as obtained as the EHR resources. The challenge questions may present a correct answer choice along with incorrect choices may be presented (e.g., multiple choice question). At 2220 and 2222, in an interactive way, the challenge questions and answers may be sent and received between the client system 104 and the value-added certificate authorization system 160.

At 2224, a verification score may be calculated based at least in part on the accuracy of the user's answers as verified against the EHR personal identification information. For example, this score may be the total number of correct answers. Alternatively, the score may be the percentage of correct answers, or any other suitable metric related to the user's performance in correctly answering questions related to his or her personal information. At 2226, based at least in part on the verification score, the user may be in one or more states, such as verified, rejected, or more challenge questions. In this way, if more challenge questions are needed to either verify or reject the user, then at 2228, more challenge questions may be asked and answers received to determine update verifications scores therefrom.

If the user is verified, then at 2230, the value-added certificate authorization system(s) 160 may provide a verified claim of identity to the client system 104 on behalf of the user 102. In some cases, the verified claim of identity may include a signed verifiable credential. Thus, the value-added certificate authorization system(s) 160 may digitally sign the assertion of identity of the user 102 associated with the client system 104.

At 2232, value-added certificate authorization system(s)) 160 may register the verified claim of identity with the blockchain system(s) 180. The registration of the verified credential may allow the client system 104 to interact with the blockchain system(s) 180, such as to set permissions to EHRs and/or to obtain access tokens to access EHRs from the resource system(s) 150.

At 2234, if the user was rejected based at least in part on the verification score, then that may be indicated to the client system. In some cases, the method 2200 may be repeated to attempt to verify a user's self-asserted identity.

It should be understood that the disclosure, as described herein, results in a variety of technical improvements in data security, information management, and computing. These technological improvements include an improved security of sensitive information, such as in the form of patient healthcare information. Additionally, the mechanisms, as discussed herein, provide for a patient to set permissions for his or her healthcare information in a secure manner. The mechanisms, as described, allows a patient to have improved control over his or her own personal information, even when that information resides at a remote location. Additionally, the mechanisms, as discussed here, allow for permissions associated with a sensitive information to reside and be logged securely on a blockchain, while the sensitive information itself may reside at a location associated with the generation and/or logging of that sensitive information. Such a mechanism of permission management, storage, and access present technical benefits, such as more efficient deployment of computing resources, efficient deployment of computing bandwidth, and efficient deployment of network bandwidth, while the storage of the sensitive data, such as the private healthcare data, may be made more secure.

Although example embodiments, as discussed above are in the context of healthcare information, it should be noted that the technologies discussed herein may be applied in a wide array of applications where shared and/or personal information is present. In fact, the technologies described above may be particularly used in situations where a party may have agency in what, who, when, where, and under what conditions to share his or her personal information. For example, the techniques described above may be used in a variety of applications, such as finance to secure and control access to financial information, in business applications to secure and control access to sensitive, non-market information, in governmental applications to secure and control access to government information. Indeed, the aforementioned list of applications are just examples, and the technologies discussed herein may be applied to a wide array of applications.

As an example of securing financial information, consider an individual who wishes to secure access to his or her financial documents (e.g., W2 forms, W4 forms, 1099 forms, K-corporation forms, brokerage statements, bank statements, tax return forms, etc.). This individual may establish a self-sovereign identity (CSI) according to the disclosure herein. This CSI may enable the individual to have agency over his or her financial records. The individual may then specify who, and under what conditions, other individuals may access his or her financial records. This permission may then be memorialized onto a permission blockchain according to embodiments disclosed herein. Users, such as a financial advisor, who wish to access the individual's financial records may then receive access tokens, as generated by smart contracts incorporated in the permission blockchain use those access tokens to access protected financial information associated with the individual from a repository of that financial information, such as the individual's bank or brokerage.

Although the subject matter presented herein has been described in language specific to computer structural features, methodological acts, and computer readable media, it is to be understood that the present disclosure is not necessarily limited to the specific features, acts, or media described herein. Rather, the specific features, acts and mediums are disclosed as example forms.

Although the methods as described with reference to the flow diagram illustrated in FIGS. 12-17, 20 and 21, many other operations for performing the acts associated with the methods may be used. For example, the order of the operations may be changed, some of the operations described may be optional, and additional operations may be included, in accordance with example embodiments of the disclosure. For example, smart contracts within the blockchain system could be configured to other blockchain-based systems thus endowed the network with limitless applications use case potential.

The subject matter described above is provided by way of illustration only and should not be construed as limiting. Various modifications and changes can be made to the subject matter described herein without following the example configurations and applications illustrated and described, and without departing from the true spirit and scope of the present invention.

The disclosure is described above with reference to block and flow diagrams of systems, methods, apparatuses, and/or computer program products according to example embodiments of the disclosure. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the disclosure.

These computer-executable program instructions may be loaded onto a general-purpose computer, a special-purpose computer, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the disclosure may provide for a computer program product, comprising a computer usable medium having a computer readable program code or program instructions embodied therein, said computer readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of mechanisms for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

It will be appreciated that each of the memories and data storage devices described herein can store data and information for subsequent retrieval. The memories and databases can be in communication with each other and/or other databases, such as a centralized database, or other types of data storage devices. When needed, data or information stored in a memory or database may be transmitted to a centralized database capable of receiving data, information, or data records from more than one database or other data storage devices. In other embodiments, the databases shown can be integrated or distributed into any number of databases or other data storage devices.

Many modifications and other embodiments of the disclosure set forth herein will be apparent having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The disclosure, as presented herein may include a method. The method may be a computer-implemented method including receiving, by a value-added certificate authorization system comprising one or more processors, from a client system, a request to certify a self-sovereign identity certificate (SIC) for access to a healthcare blockchain; requesting, by the value-added certificate authorization system, and from the client system, a plurality of personal identification information associated with the SIC; receiving, by the value-added certificate authorization system, the plurality of personal identification information; requesting, by the value-added certificate authorization system, from an independent identity authority system, verification of the plurality of personal identification information; verifying, by the value-added certificate authorization system, the plurality of personal identification information; and certifying, by the certificate authorization system, responsive to the verification, the SIC as a certified sovereign identity (CSI), wherein the CSI authorizes the client system to access the healthcare blockchain. In example embodiments, the method may further comprise registering the CSI with the healthcare blockchain by instructing an inclusion of a public key associated with the CSI on the healthcare blockchain. In further example embodiments, the CSI comprises a public key that is included in the healthcare blockchain and a private key that is stored on the client system.

In some example embodiments, the method may include receiving, by the value-added certificate authorization system, from an application download system, a request to bind the CSI to a healthcare application; and instructing, responsive to the request to bind the CSI to the healthcare application, storing the CSI in a digital wallet of the client system. In still further example embodiments, the method may be wherein the CSI is a first CSI, the first CSI corresponding to a first user, the method further comprising: receiving a request to grant a permission for a health information resource to a second user, the second user having a second CSI; determining, based at least in part on the first CSI, that the first user is authorized to set permissions for the health information resource; and instructing, a blockchain system, to include a smart contract corresponding to the grant of the permission to the second user for the health information resource. In yet further example embodiments, the grant of the permission for the health information resource comprises one or more conditions under which the second user is permitted to access the health record. Further still, in example embodiments, the client system is a first client system, and wherein the smart contract comprises instructions to issue an access token to the second user, the access token allowing a second client system corresponding to the second user to receive the health information resource from a resource server.

According to example embodiments of the disclosure, there may be a system including a memory that stores computer-executable instructions; at least one processor configured to access the memory, wherein the at least one processor is further configured to execute the computer-executable instructions to: receive, from a client system, a request to certify a self-sovereign identity certificate (SIC) for access to a healthcare blockchain; request, from the client system, a plurality of personal identification information associated with the sovereign identity; receive the plurality of personal identification information; request, from an independent identity authority system, verification of the plurality of personal identification information; verify the plurality of personal identification information; and certify, responsive to the verification, the SIC as a certified sovereign identity (CSI), wherein the CSI authorizes the client system to access the healthcare blockchain. In example embodiments, the at least one processor is further configured to execute the computer-executable instructions to register the CSI with the healthcare blockchain. In further example embodiments, the CSI comprises a public key that is included in the healthcare blockchain and a private key that is stored on the client system. In additional example embodiments, the at least one processor is further configured to execute the computer-executable instructions to: receive, from an application download system, a request to bind the CSI to a healthcare application; and instruct, responsive to the request to bind the CSI to the healthcare application, storing the CSI in a digital wallet of the client system.

According to some example embodiments, the system is such that the CSI is a first CSI, the first CSI corresponding to a first user, and wherein the at least one processor is further configured to execute the computer-executable instructions to: receive a request to grant a permission for a health information resource to a second user, the second user having a second CSI; determine, based at least in part on the first CSI, that the first user is authorized to set permissions for the health information resource; and instruct, a blockchain system, to include a smart contract corresponding to the grant of the permission to the second user for the health information resource. In further example embodiments, the grant of the permission for the health information resource comprises one or more conditions under which the second user is permitted to access the health information resource. In still further example embodiments, the client system is a first client system, and wherein the smart contract comprises instructions to issue an access token to the second user, the access token allowing a second client system corresponding to the second user to receive the health information resource from a resource server.

According to example embodiments of the disclosure, there are one or more non-transitory computer-readable media maintaining instructions executable by one or more processors to perform operations comprising: identifying that access to a healthcare blockchain is to be established on behalf of a first user; generate a self-sovereign identity certificate (SIC) associated with the first user; sending, to a value-added certificate authorization system, a request to certify the SIC for access to a healthcare blockchain; receiving a request for a plurality of personal identification information associated with the first user; receiving the plurality of personal identification information; sending, to the value-added certificate authorization system, the plurality of personal identification information; receiving an indication of certification of the SIC as a certified sovereign identity (CSI), wherein the CSI authorizes to access the healthcare blockchain.

In example embodiments, the operations further comprise: receiving, a healthcare application; requesting, the value-added certificate authorization system, to bind the CSI to the healthcare application; receiving instructions to store the CSI in a digital wallet associated with the healthcare application; and storing the CSI in the digital wallet of the healthcare application. In further example embodiments, the operations further comprise: requesting setting a first permission for a first healthcare record for a second user associated with a second CSI; and receiving confirmation that the first permission is set, wherein the confirmation indicates that a smart contract corresponding to the first permission has been added to the healthcare blockchain. In still further example embodiments, the first permission is a conditional permission. In yet further example embodiments, the operations further comprise: generate a verification request for a healthcare information resource; send the verification request to a blockchain system; receive an access token corresponding to the healthcare information resource; generate a request for the healthcare information resource; send, to a resource server, the request for the healthcare information resource and the access token; and receive, the healthcare information resource. In some example embodiments, the healthcare information resource is received in a predetermined format, and wherein the operations further comprise displaying the healthcare information resource.

What is claimed is:

1. A computer-implemented method, comprising:
   receiving, by a client systems module of a value-added certificate authorization system comprising one or more processors, from a client system, a request to verify a claimed identity of a user;
   requesting, by the client systems module of the value-added certificate authorization system, and from a first resource system, a first health information resource (HIR) associated with the user;
   receiving, by the client systems module of the value-added certificate authorization system and responsive to the request for the first HIR, the first HIR;
   generating, by an identity authority module of the value-added certificate authorization system, a first challenge question based at least in part on the first HIR
   determining an answer to the first challenge question based at least in part on the first HIR;
   generating at least one false answer choice to the first challenge question;
   sending, by the value-added certificate authorization system and to the client system, the first challenge question and one or more answer choices including the answer and the at least one false answer choice;
   receiving, by the value-added certificate authorization system and from the client system, a first answer to the first challenge question;
   determining, by a certified sovereign identity (CSI) key module of the value added certificate authorization system and based at least in part on the first answer, that the user is to be verified; and providing, by the certified sovereign identity (CSI) key module of the value-added certificate authorization system and based at least in part on the determining that the user is to be verified, a signed verified credential.

2. The computer-implemented method of claim 1, further comprising registering the signed verified credential with a healthcare blockchain, wherein the registering the signed verified credential allows the user to access the healthcare blockchain.

3. The computer-implemented method of claim 1, further comprising:
identifying, based at least in part on the request to verify the claimed identity, the first resource system, wherein the first resource system stores the first HIR.

4. The computer-implemented method of claim 1, further comprising:
determining, based at least in part on the request to verify the claimed identity, an initial set of challenge questions;
determining, based at least in part on receiving the first HIR, a final set of challenge questions, the final set of challenge questions including the first challenge question.

5. The computer-implemented method of claim 1, wherein determining that the user is to be verified further comprises:
determining a score based at least in part on the first answer; and
determining that the score is greater than a threshold value.

6. The computer-implemented method of claim 1, further comprising:
requesting, by the value-added certificate authorization system, and from the first resource system, a second HIR associated with the user;
receiving, by the value-added certificate authorization system and responsive to the request for the second HIR, the second HIR;
generating a second challenge question based at least in part on the second HIR;
sending, to the client system, the second challenge question; and
receiving, from the client system, a second answer to the second challenge question, wherein determining that the user is to be verified is based at least in part on the second answer to the second challenge question.

7. A system, comprising:
a memory that stores computer-executable instructions;
at least one processor configured to access the memory, wherein the at least one processor is further configured to execute the computer-executable instructions to:
receive, by a client systems module and from a client system, a request to verify a claimed identity of a user;
request, from one or more resource systems, one or more electronic health information resources (HIRs) associated with the user;
receive, responsive to the request for the one or more HIRs, individual ones of the HIRs;
generate one or more challenge questions based at least in part on the individual ones of the HIRs;
send, to the client system, the one or more challenge questions;
receive, from the client system, one or more answers to individual ones of the one or more challenge questions;

determine, by a certified sovereign identity (CSI) key module based at least in part on the one or more answers, that the user is to not be verified; and
provide, based at least in part on the determining that the user is not to be verified, an indication that the claimed identity was not verified.

8. The system of claim 7, wherein the at least one processor is further configured to:
identify, based at least in part on the request to verify the claimed identity of the user, a the one or more resource systems.

9. The system of claim 7, wherein to request the one or more HIRs associated with the user comprises the at least one processor is further configured to execute the computer-executable instructions to:
generate an access token corresponding to each of the one or more HIRs.

10. The system of claim 7, wherein to generate one or more challenge questions based at least in part on the individual ones of the HIRs, the at least one processor is further configured to execute the computer-executable instructions to:
determine an initial one or more challenge questions; and
revise the initial one or more challenge questions based at least in part on the individual ones of the HIRs.

11. The system of claim 7, wherein to generate one or more challenge questions comprises the at least one processor is further configured to execute the computer-executable instructions to:
determine an answer to each of the one or more challenge questions based at least in part on the one or more HIRs; and
generating at least one false answer choice for each of the one or more challenge questions.

12. The system of claim 7, wherein the at least one processor is further configured to execute the computer-executable instructions to:
receive a second request to verify a second claimed identity of a second user;
request, from a second one or more resource systems, a second one or more HIRs associated with the second user;
receive, responsive to the request for the second one or more HIRs, individual ones of the second HIRs;
generate a second one or more challenge questions based at least in part on the individual ones of the second HIRs;
send the second one or more challenge questions;
receive, from the client system, a second one or more answers to the individual ones of the second one or more challenge questions;
determine, based at least in part on the second one or more answers, that the second user is to be verified; and
providing, based at least in part on the determining that the second user is to be verified, a signed verified credential.

13. The system of claim 12, wherein the at least one processor is further configured to execute the computer-executable instructions to:
register the signed verified credential with a healthcare blockchain, wherein the registering the signed verified credential allows access by the second user to access the healthcare blockchain.

14. The system of claim 12, wherein to determine that the second user is to be verified the at least one processor is further configured to execute the computer-executable instructions to:

determine a score based at least in part on the second one or more answers; and determining that the score is greater than a threshold value.

15. One or more non-transitory computer-readable media maintaining instructions executable by one or more processors to perform operations comprising:

receiving, by a client systems module of a value-added certificate authorization system comprising one or more processors, from a client system, a request to verify a claimed identity of a user;

requesting, by the value-added certificate authorization system, and from a first resource system, a first health information resource (HIR) associated with the user;

receiving, by the value-added certificate authorization system and responsive to the request for the first HIR, the first HIR;

generating a first challenge question based at least in part on the first HIR;

sending, to the client system, the first challenge question;

receiving, from the client system, a first answer to the first challenge question;

determining, based at least in part on the first answer, that the user is to be verified; and providing, by a certified sovereign identity (CSI) key module based at least in part on the determining that the user is to be verified, a signed verified credential.

16. The one or more non-transitory computer-readable media of claim 15, wherein the operations further comprise:

registering the signed verified credential with a health care blockchain, wherein the registering the signed verified credential allows the user to access the healthcare blockchain.

17. The one or more non-transitory computer-readable media of claim 15, wherein the operations further comprise:

identifying, based at least in part on the request to verify the claimed identity, the first resource system, wherein the first resource system stores the first HIR.

18. The one or more non-transitory computer-readable media of claim 15, wherein the operations further comprise:

determining, based at least in part on the request to verify the claimed identity, an initial set of challenge questions; and determining, based at least in part on receiving the first HIR, a final set of challenge questions, the final set of challenge questions including the first challenge question.

19. The one or more non-transitory computer-readable media of claim 15, wherein the operations further comprise:

determining an answer to the first challenge question based at least in part on the first HIR; and generating at least one false answer choice to the first challenge question.

* * * * *